(12) United States Patent
Gaillard et al.

(10) Patent No.: US 10,945,966 B2
(45) Date of Patent: *Mar. 16, 2021

(54) PEGYLATED LIPID NANOPARTICLE WITH BIOACTIVE LIPOPHILIC COMPOUND

(71) Applicant: Eyesiu Medicines B.V., Leiden (NL)

(72) Inventors: Pieter Jaap Gaillard, Leiden (NL); Jacob Rip, Leiden (NL)

(73) Assignee: Eyesiu Medicines B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/681,908

(22) Filed: Nov. 13, 2019

(65) Prior Publication Data
US 2020/0163898 A1    May 28, 2020

Related U.S. Application Data

(62) Division of application No. 15/751,170, filed as application No. PCT/EP2016/069107 on Aug. 11, 2016, now Pat. No. 10,525,012.

(30) Foreign Application Priority Data

Aug. 11, 2015 (NL) ..................................... 2015291

(51) Int. Cl.
*A61K 9/51* (2006.01)
*A61K 49/00* (2006.01)
(Continued)

(52) U.S. Cl.
CPC .......... *A61K 9/5123* (2013.01); *A61K 9/0048* (2013.01); *A61K 9/1271* (2013.01);
(Continued)

(58) Field of Classification Search
CPC .. A61K 9/5123; A61K 9/1271; A61K 9/0048; A61K 31/4356; A61K 31/00;
(Continued)

(56) References Cited

U.S. PATENT DOCUMENTS 9,265,782 B2 * 2/2016 Robledo .............. A61K 9/0048
2002/0013271 A1   1/2002 Parikh
(Continued)

FOREIGN PATENT DOCUMENTS

JP     2006508126 A    3/2006
JP     2013503855 A    2/2013
(Continued)

OTHER PUBLICATIONS

Remsberg, Connie M. et al. "Pharmacokinetic Evaluation of a DSPE-PEG2000 Micellar Formulation of Ridaforolimus in Rat." Pharmaceutics 5.1 (2013): 81-93. PMC.
(Continued)

*Primary Examiner* — Carlos A Azpuru
(74) *Attorney, Agent, or Firm* — NLO; Catherine Shulz; Tamara Stegmann

(57) ABSTRACT

The invention relates to nanoparticles for the systemic or topical delivery of lipophilic diagnostic or therapeutic agents to a subject in need thereof. The nanoparticles of the invention comprise a water soluble polymer and at least one of a biocompatible lipid and a lipophilic agent. The invention further relates to ophthalmic treatment using the nanoparticles of the invention. In addition, the invention pertains to compositions and formulations comprising the nanoparticle of the invention. Such formulation may be an eye drop formulation.

8 Claims, 2 Drawing Sheets

(51) Int. Cl.

| | | |
|---|---|---|
| *A61K 9/127* | (2006.01) | |
| *A61K 47/69* | (2017.01) | |
| *A61K 31/436* | (2006.01) | |
| *A61K 31/00* | (2006.01) | |
| *A61P 27/02* | (2006.01) | |
| *A61K 9/00* | (2006.01) | |
| *A61K 31/164* | (2006.01) | |
| *A61K 38/13* | (2006.01) | |
| *B82Y 5/00* | (2011.01) | |

(52) U.S. Cl.
CPC ............ *A61K 31/00* (2013.01); *A61K 31/164* (2013.01); *A61K 31/436* (2013.01); *A61K 38/13* (2013.01); *A61K 47/6929* (2017.08); *A61K 47/6935* (2017.08); *A61K 49/0041* (2013.01); *A61K 49/0093* (2013.01); *A61P 27/02* (2018.01); *B82Y 5/00* (2013.01)

(58) Field of Classification Search
CPC .. A61K 31/164; A61K 38/13; A61K 47/6929; A61K 47/6935; A61K 49/0041; A61K 49/0093; B82Y 5/00
See application file for complete search history.

(56) References Cited

U.S. PATENT DOCUMENTS

| | | | |
|---|---|---|---|
| 2002/0119199 | A1 | 8/2002 | Parikh |
| 2004/0245662 | A1* | 12/2004 | Chaubal ................. A61K 9/10 264/5 |
| 2009/0074828 | A1 | 3/2009 | Alexis |
| 2011/0064800 | A1 | 3/2011 | Jenkins |
| 2015/0132369 | A1 | 5/2015 | Rezayat et al. |

FOREIGN PATENT DOCUMENTS

| | | | |
|---|---|---|---|
| JP | 2013507337 | A | 3/2013 |
| JP | 2014527532 | A | 10/2014 |
| JP | 2015511239 | A | 4/2015 |
| WO | WO98/07414 | A1 | 2/1998 |
| WO | WO01/17546 | A1 | 3/2001 |
| WO | WO2006/002540 | A1 | 1/2006 |
| WO | WO2010/146606 | A1 | 12/2010 |
| WO | WO2011/017548 | A1 | 2/2011 |
| WO | 201507837 | * | 5/2015 |
| WO | WO2015/071837 | A1 | 5/2015 |

OTHER PUBLICATIONS

Vakil, Ronak, et al. "Combination antifungal therapy involving amphotericin B, rapamycin and 5-fluorocytosine using PEG-phospholipid micelles." Pharmaceutical research 25.9 (2008): 2056-2064.

Mishra Gyan P., et al. "Recent applications of liposomes in ophthalmic drug delivery." Journal of drug delivery 2011 (2011). 2011:863734.

Di Tommaso, Claudia, et al. "A novel cyclosporin a aqueous formulation for dry eye treatment: in vitro and in vivo evaluation." Investigative ophthalmology & visual science 53.4 (2012): 2292-2299.

Lallemand, Frederic, et al. "Successfully improving ocular drug delivery using the cationic nanoemulsion, novasorb." Journal of drug delivery 2012 (2012).2012:604204.

Agrawal, Sarita "A review on novel therapeutic strategies for the enhancement of solubility for hydrophobic drugs through lipid and surfactant based self micro emulsifying drug delivery system: a novel approach." Am. J. Drug Disc. Develop 2.4 (2012): 143-183.

International Search Report issued in International Patent Application No. PCT/EP2016/069107 dated Oct. 24, 2016.

* cited by examiner

PEGYLATED LIPID NANOPARTICLE WITH BIOACTIVE LIPOPHILIC COMPOUND

FIELD OF THE INVENTION

The present invention relates to the fields of medicine and pharmacy. In particular the invention relates to the field of drug formulation. The invention relates to nanoparticles with or without a diagnostic or therapeutic agent and comprise a biocompatible lipid and a water soluble polymer. The nanoparticles of the invention can be used for the administration of (highly) lipophilic agents, such as acylethanolamides and/or immunomodulatory macrolides (macrocyclic lactones) like cyclosporines, tacrolimus and/or sirolimus. Preferably, the stable, inert, clear and solvent-free nanoparticles of the invention can be used for ophthalmological, topical or systemic treatments.

BACKGROUND OF THE INVENTION

A major hurdle for the development of drug formulations is the hydrophobic nature of many therapeutic compounds, which hampers the solubility and bioavailability of a drug. To overcome this limitation, numerous new drug formulations are explored, such as liposomes, micelles and emulsions.

Examples of such lipophilic therapeutic compounds are macrolides, such as cyclosporine (e.g. cyclosporine A (CsA)), rapamycin/sirolimus (RAP or SIR) and FK506/tacrolimus (TAC), or the like, such as everolimus, ridaforolimus, temsirolimus, umirolimus, zotarolimus, ascomycin, FK1012 or pimecrolimus, or structurally related compounds, or palmitoylethanolamide (PEA).

CsA is an immunosuppressant agent widely used in organ transplantation to prevent rejection. It reduces the activity of the immune system by interfering with the activity and growth of T-cells. In particular, CsA binds to the cytosolic protein cyclophilin (immunophilin) present in lymphocytes, especially T-cells. This complex of cyclosporin and cyclophilin subsequently inhibits calcineurin, which is responsible for activating the transcription of interleukin 2 and related cytokines. Cyclosporine also inhibits lymphokine production and interleukin release and, therefore, reduces the function of effector T-cells.

The first oral CsA formulation introduced into clinical use (Sandimmune) comprised a solution of CsA dissolved in a solvent system of olive oil and ethanol (Patentschrift (Switz.) CH 641 356, Feb. 29, 1984, Appl. 79/1949. Feb. 27, 1979). The oil was emulsified in water using a polyethoxylated oleic glyceride surfactant to give a coarse O/W emulsion. This system was found to be inherently thermodynamically unstable. As a result, the drug tended to precipitate out of solution, and thus not be absorbed.

As described for CsA above, similar thermodynamically unstable solutions, leading to drug precipitation are known to occur for other macrolides, such as rapamycin/sirolimus and FK506/tacrolimus, or the like, such as everolimus, ridaforolimus, temsirolimus, umirolimus, zotarolimus, ascomycin, FK1012 or pimecrolimus, or structurally related compounds.

Solvent-free formulations with relatively high concentrations of rapamycin and ridaforolimus using micelles with PEG-phospholipid conjugates (such as DSPE-PEG$_{2000}$) have been described in the art (Remsberg et al., Pharmaceutics 2013, 5, 81-93; Vakil et al., Pharm. Res. 2008, 25, 2056-2064), as well as for a large range of other lipophilic drugs such as palmitoylethanolamide (PEA), miconazole, paclitaxel, docetaxel, nelfinavir mesylate, propofol, diazepam and ixabepilone. However, all these formulations were found to be thermodynamically unstable, both at storage conditions and (once diluted below the critical micelle concentration) in biological fluids. In fact, Remsberg et al. (supra) described that: "For unclear reasons, solubilization of ridaforolimus in DSPE-PEG$_{2000}$ micelles did not dramatically increase the residence time or the overall systemic exposure of ridaforolimus. This may be indicative of a lack of in vivo stability or an inability to evade the mononuclear phagocyte system." In addition, Vakil et al. (supra) demonstrated that the micellar rapamycin formulation: "however, had no significant effect of the pharmacokinetic disposition of rapamycin with only a longer $t_{1/2}$ being significant." These results are in accordance with the results found in the Remsberg at al. (supra) study. There clearly is a need in the art for a stable formulation for immunomodulatory macrolides, e.g. in biological fluids, as well as under storage conditions.

The lipophilic agent PEA is a fatty acid amide that occurs naturally in humans, and belongs to the class of nuclear factor agonists. PEA has been demonstrated to bind to a nuclear receptor and exerts a great variety of biological functions related to chronic pain and inflammation. Currently, the only available form of this lipophilic drug is micronized, ultramicronized or a cyclodextrin-entrapped form. For example, the ultra-micronized form of palmitoylethanolamide, gives rise to high plasma levels of a metabolite of palmitoylethanolamide, 2-arachidonoylglycerol (2-AG), which is known to be less effective than PEA for the treatment of chronic pain and inflammation.

Delivery of lipophilic drugs such as macrolides (e.g. CsA and/or SIR and/or TAC) and/or PEA to the eye is especially challenging, due to the unique protective mechanisms of the eye. In particular, there are three barriers to ocular penetration: The corneal epithelium, the blood-aqueous barrier and the blood-retinal barriers.

The common routes of drug administration for the treatment of eye disorders are topical, systemic, periocular and intravitreal. Topical administration is the most preferred route because of the highest patient compliance and the least invasive nature. Upon topical administration, absorption of a drug takes place either through the corneal route (cornea, aqueous humor, intraocular tissues) or noncorneal route (conjunctiva, sclera, choroid/retinal pigment epithelium (RPE)). Only a small fraction of the topically applied drugs, generally less than 5%, reaches the intraocular tissues (Mishra G P et al. J. of Drug Delivery (2011) 2011:863734). Factors responsible for poor ocular bioavailability following topical instillation are precorneal drainage and the lipoidal nature of the corneal epithelium. In addition, a major fraction of the drug reaches the systemic circulation through conjunctival vessels and the nasolacrimal duct, which can lead to severe adverse effects. Hence, the topical route has only been successful to a limited extent so far.

Systemic administration requires the administration of high doses due to the blood-aqueous barrier and blood-retinal barrier. Such high doses can lead to severe side effects. Furthermore, intravitreal administration requires frequent administration, which may cause susceptibility for vitreous haemorrhage, retinal detachment and endophthalmitis. Thus there is a clear need to improve the delivery of drugs to the eye.

The lipophilic drug cyclosporine A (CsA) has been explored for dry eye syndrome, autoimmune uveitis and the prevention of corneal graft rejection. CsA has also been investigated for treating several eye infections, such as posterior blepharitis, atopic keratoconjunctivitis and herpetic stromal keratitis (DiTommaso et al. Invest Ophthalmol. Vis. Sci. (2012) 53(4):2292-9). For many of these diseases, high systemic concentrations of CsA have to be administered to reach therapeutic ocular drug levels, resulting in serious side effects, such as nephrotoxicity and hypertension. Hence, a topical and local CsA administration would be favourable.

Restasis (Allergen, Irvin, Calif.) is an ophthalmic emulsion comprising CsA for dry eye treatment. Restasis is a white opaque to slightly translucent homogeneous emulsion comprising 0.05% CsA. The CsA is formulated in a polyoxyethylene castor oil (Cremophor EL).

Cremophor EL is responsible for a painful burning or stinging sensation after application of eye drops, as well as for e.g. infusion reactions after intravenous applications. These side effects caused by Cremophor EL limit the dosing amount and frequency. Furthermore, the low formulation strength and rapid clearance from the eye or body requires continued dosing to be effective, further leading to poor patient compliance. Cremophor is a commonly used emulsifier for lipophilic drugs. For example, the drugs miconazole, paclitaxel, docetaxel, nelfinavir mesylate, propofol, diazepam, vitamin K and ixabepilone are usually formulated in a polyoxyethylene castor oil (Cremophor EL).

Cyclokat and Vekacia are two other ophthalmic emulsions, which are based on a cationic technology called Novasorb (Novagali Pharma, France). The concentration CsA in these emulsions is 0.1% (Lallemand et al. J. Of Drug Delivery (2012): 2012:604204). The formulation CyclASol (Novaliq) is based on Semi-Fluorinated Alkanes (SFAs) and comprises 0.05% CsA.

Yet, other formulations containing a higher concentration of CsA comprise a lipid or fat milky (IntraLipid) emulsion of 5 mg/mL CsA (0.5%). Such emulsions are ready to be used intravenously and are currently explored for cardiac and brain disorders (CicloMulsion® and NeuroSTAT®). Locally used formulations are however prepared in dimethyl sulfoxide (DMSO), which is also quite toxic to cells and tissues.

The lipophilic agent PEA is currently used in eye drops in veterinary medicine for its soothing activity (Oculvet Drops). In addition, a clinical study has demonstrated that oral administration of PEA was effective in reducing the increased intraocular pressure (IOP) after the iridotomy procedure. In another clinical trial, PEA was found to significantly reduce IOP in patients diagnosed with primary open-angle glaucoma (POAG) or with ocular hypertension and it seems that PEA increases aqueous humor outflow through the trabecular meshwork (TM) pathway (Kumar et al).

Besides the delivery of diagnostic or therapeutic lipophilic agents to the eye, eye drops may also be used for the treatment of dry and irritated eyes. In such case, the eye drop formulation does not need to comprise an active lipophilic agent, but comprises ingredients to lubricate and soothe the irritated eye. Such eye drop formulations are commonly known as artificial tears. Notably, there is currently no stable artificial tear formulation available in the art that is clear, comprises naturally occurring soothing lipids and is also moisturizing to the eye.

There is thus still a need in the art for improved (stable, inert, clear and solvent-free) formulations of lipophilic agents (such as immunomodulatory macrolides) for the systemic or topical administration of an effective concentration of such agents. In particular, there is a need in the art for such formulations for the treatment or alleviation of a skin, mucosal or eye disease or disorder, without causing (severe) side effects at the site of administration.

SUMMARY OF THE INVENTION

In a first aspect the invention pertains to a nanoparticle comprising at least one of: a) a biocompatible lipid; and, b) a lipophilic therapeutic, lubricating and/or diagnostic agent, wherein the nanoparticle has a surface comprising a water soluble polymer.

In a preferred embodiment, the lipophilic agent is at least one of an acylethanolamide and a macrolide.

More preferably, the macrolide is selected from the group consisting of cyclosporine, sirolimus, tacrolimus, everolimus, ridaforolimus, temsirolimus, umirolimus, zotarolimus, ascomycin, FK1012 and pimecrolimus, or a derivative or analog thereof, preferably wherein the macrolide is cyclosporine, sirolimus, or tacrolimus. Preferably, the cyclosporine is selected from the group consisting of cyclosporine A (CsA), CsA form 2, cyclosporine B, C, D, E, F, G, H, I, J, K, L, M, N, O, P, Q, R, S, T, U, V, W, X, Y, Z, Voclosporine, Valspodar (PSC833), SCY-635, NIM811 and Debio-025. Most preferably, the cyclosporine is cyclosporine A.

In yet another preferred embodiment, the acylethanolamide comprises at least one of palmitoylethanolamide (PEA), oleoylethanolamide (OEA), 2-arachidonylglycerol (2-AG), anandamide (AEA) and an AEA derivative selected from the group consisting of JWH-018, JWH-073, CP-55940, Dimethylheptylpyran, HU-210, HU-331, SR144528, WIN 55,212-2, JWH-133, Levonantradol (Nantrodolum), adelmidrol and AM-2201. Most preferably, the acylethanolamide is palmitoylethanolamide (PEA).

In another preferred embodiment, the biocompatible lipid comprises one or more phospholipids. Preferably, the one or more phospholipids are neutral phospholipids. More preferably, the biocompatible lipid comprises one or more neutral phospholipids selected from the group consisting of 1,2-dilauroyl-sn-glycero-3-phosphate (DLPA), 1,2-dilauroyl-sn-glycero-3-phosphoethanolamine (DLPE), 1,2-dimyristoyl-sn-glycero-3-phosphate (DMPA), 1,2-dimyristoyl-sn-glycero-3-phosphocholine (DMPC), 1,2-dimyristoyl-sn-glycero-3-phosphoethanolamine (DMPE), 1,2-dimyristoyl-sn-glycero-3-phosphoglycerol (DMPG), 1,2-dimyristoyl-sn-glycero-3-phosphoserine (DMPS), 1,2-dipalmitoyl-sn-glycero-3-phosphate (DPPA), 1,2-dipalmitoyl-sn-glycero-3-phosphocholine (DPPC), 1,2-dipalmitoyl-sn-glycero-3-phosphoethanolamine (DPPE), 1,2-dipalmitoyl-sn-glycero-3-phosphoglycerol (DPPG), 1,2-dipalmitoyl-sn-glycero-3-phosphoserine (DPPS), 1,2-distearoyl-sn-glycero-3-phosphate (DSPA), 1,2-distearoyl-sn-glycero-3-phosphocholine (DSPC), 1,2-distearoyl-sn-glycero-3-phosphoethanolamine (DSPE), 1,2-distearoyl-sn-glycero-3-phosphoglycerol (DSPG), 1,2-distearoyl-sn-glycero-3-phosphoserine (DSPS) and hydrogenated soy phosphatidylcholine (HSPC). Even more preferably, the one or more neutral phospholipids comprise at least one of HSPC and DSPE. Most preferably, the one or more neutral phospholipids comprise at least HSPC.

In a further embodiment of the invention, the water soluble polymer is conjugated to at least one of the biocompatible lipid and the lipophilic therapeutic or diagnostic agent. Preferably, the water soluble polymer is conjugated to the biocompatible lipid.

In an embodiment of the invention, the water soluble polymer is at least one of: i) a polyalkylether, preferably the polyalkylether is linear polyethylene glycol (PEG), star PEG or multi-arm branched PEG; ii) a homopolymer that is a PEG substitute or a PEG alternative, preferably the homopolymer is selected from the group consisting of polymethylethyleneglycol (PMEG), polyhydroxypropyleneglycol (PHPG), polypropyleneglycol (PPG), polymethylpropyleneglycol (PMPG), polyhydroxypropyleneoxide (PHPO), poly-oxazoline (POZ) and hydroxyethyl starch (HES); iii) a heteropolymer of small alkoxy monomers, preferably the heteropolymer comprises polyethyleneglycol/polypropyleneglycol (PEG/PPG). Preferably, the water soluble polymer has a molecular weight of at least about 120 Daltons and a polymerization number of at least 6 or about 6-210.

In a particular embodiment of the invention, the conjugate of the biocompatible lipid and the water soluble polymer is a conjugate of a phospholipid as defined above, Vitamin E or a derivative of Vitamin E, to a polymer as defined above. Preferably, the conjugate is a 1,2-distearoyl-sn-glycero-3-phosphoethanolamine-N-polyethylene glycol (DSPE-PEG). More preferably, the conjugate is 1,2-distearoyl-sn-glycero-3-phosphoethanolamine-N-[methoxy(polyethylene glycol)-2000 (DSPE-mPEG2000) or d-alpha tocopheryl-N-[methoxy(polyethylene glycol)-1000 (TPEG1000).

In an embodiment of the invention, the size of the nanoparticle is between 5-300 nm, preferably the size of the nanoparticle is between 10 and 150 nm.

In a second aspect, the invention pertains to a composition comprising a nanoparticle as defined herein and an excipient or carrier that is suitable for human or veterinary use. Preferably, the composition is a pharmaceutical composition. Preferably, the composition is a clear aqueous solution comprising at least 0.5%, 1%, 5% or 10% (w/w) of the lipophilic therapeutic or diagnostic agent. More preferably, the composition has a turbidity that is not higher than 40, 20, 10, 5, 2 or 1 FTU as determined according to the ISO 7027:1999 standard.

In a preferred embodiment, the composition is in a formulation selected from the group consisting of a cream, an ointment, a gel, a solution for spray delivery, an eyewash, a liniment, a patch, a lotion, a wipe, a pad, a towelette, an eye wipe, an eye drop, an ear drop, a solid dosage form, a capsule, a tablet, (freeze-dried) powders or tablet, a dry powder, an aerosolic dosage form for inhalation, nebulisation or nasal delivery, a liquid dosage form, an elixir, a syrup, and an intravenous infusion fluid.

In an embodiment of the invention, the composition further comprises a substrate for a drug efflux pump.

In a third aspect, of the invention pertains to a nanoparticle or a composition as defined herein for use as a medicament.

In a fourth aspect, the invention pertains to a nanoparticle or a composition as defined herein for use in the prevention or treatment of a pathology, condition or disorder associated with: a) pain; b) disruption of an epithelial or endothelial barrier; c) decreased blood pressure; d) decreased local vascular blood flow; e) decreased clearance from cellular waste materials; f) mitochondria dysfunction; g) activation of the immune system; h) inflammation; i) decreased ocular humor outflow and/or other ocular diseases; j) cancer; k) neuronal disorder; l) organ rejection; m) viral diseases; n) trauma, surgery and wound healing; o) genetic diseases; p) infectious diseases; and/or q) eye diseases.

In a fifth aspect, the invention relates to a nanoparticle or a composition as defined herein for use in the prevention or treatment of a pathology, condition or disorder, wherein the nanoparticle or the composition is administrated by at least one of intravenous, intraperitoneal, intramuscular, intraarterial, intralesional, intracranial, intraocular, conjunctival, intracorneal, dermal, mucosal, ophthalmic, nasal or oral routes, wherein preferably the treatment comprises administrating by intraocular, dermal, mucosal, conjunctival or ophthalmic routes. Preferably, the administration of the nanoparticle or composition is in separate, combined or sequential administration with the substrate for a drug efflux pump.

In another aspect, the invention relates to a nanoparticle comprising a biocompatible lipid and a water soluble polymer for use in an ophthalmological treatment. Preferably, the biocompatible lipid is a lipid as defined herein. Preferably, the water soluble polymer is a polymer as defined herein.

In a preferred embodiment, ophthalmological treatment comprises the treatment or prevention of at least one of dry, injured and irritated eyes.

In another aspect, the invention pertains to an eye drop formulation, comprising a nanoparticle, a composition or formulation as defined herein.

In another aspect, the invention relates to an applicator for applying an effective amount of an eye drop formulation to an eye, wherein the applicator comprises the eye drop formulation as defined herein.

DESCRIPTION OF THE INVENTION

The current invention relates to a nanoparticle that comprises a high concentration of a lipophilic drug, which nanoparticle can be administrated without causing a painful burning or stinging sensation after topical or systemic administration. The current invention further provides for a composition comprising a nanoparticle with our without a lipophilic drug, which composition is a clear aqueous solution. It is well-known that the administration of a clear aqueous solution significantly increases patient compliance. In a first aspect, the invention therefore relates to a nanoparticle.

A nanoparticle is herein understood to be a small object that behaves as a single integer unit with respect to its transport and properties. Preferably, a nanoparticle of the invention is a solid lipid nanoparticle and the solid lipid nanoparticle preferably does not comprise any stabilizing surfactants. The size of a nanoparticle is preferably between 1 and 300 nm. A nanoparticle of the invention is preferably not a liposome. In particular, the nanoparticle of the invention does not comprise a lipid bilayer.

The nanoparticle preferably comprises at least one of:
a) a biocompatible lipid; and,
b) a lipophilic therapeutic, or diagnostic agent. The lipophilic agent may in addition or alternatively be a lubricating and/or moisturizing agent.

The nanoparticle further preferably has a surface comprising a water soluble polymer.

Preferably, the surface of the nanoparticle is at least partly covered by the water soluble polymer. More preferably, the water soluble polymer covers the surface of the nanoparticle for at least about 10, 20, 30, 40, 50, 60, 70, 80, 90, 99 or 100%. In a further embodiment, the nanoparticle has a surface consisting of a water soluble polymer.

In a preferred embodiment, the invention relates to a nanoparticle comprising a biocompatible lipid and a water soluble polymer. Preferably, the invention pertains to a nanoparticle comprising a biocompatible lipid and a water soluble polymer for use in an ophthalmological treatment.

In an alternative embodiment, the nanoparticle comprises a biocompatible lipid, a water soluble polymer and a lipophilic therapeutic, lubricating, moisturising, or diagnostic agent. In a more preferred embodiment the nanoparticle comprises a biocompatible lipid, a water soluble polymer and a lipophilic therapeutic agent.

Preferably, the therapeutic, lubricating or diagnostic agent according to the invention is at least partly lipophilic. A lipophilic therapeutic, lubricating or diagnostic agent is herein defined as the ability of the agent to dissolve in fats, oils, lipids and/or solvents such as ethanol, methanol, isopropanol, hexane or toluene. Preferably, the lipophilic agent is able to dissolve in ethanol. Alternatively, a lipophilic agent is herein defined as the inability of the agent to dissolve in water.

Preferred solvents have a dielectric constant of less than about 30. Therefore, a lipophilic agent of the invention preferably dissolves at room temperature in a solvent comprising a dielectric constant of less than about 65, 60, 55, 50, 45, 40, 35, 32, 31, 30, 29, 28, 27, 26, 25, 24, 23, 22, 21, 20, 17, 16, 15, 14, 13, 10 or 5. Preferably, the solvent is a pharmaceutically acceptable solvent.

Preferably, a lipophilic agent for use in the invention cannot or cannot easily dissolve in water. Water comprises a dielectric constant of 88 at 0° C. Therefore, a lipophilic compound for use in the invention preferably does not dissolve at room temperature in a solvent comprising a dielectric compound of at least about 28, 30, 32, 35, 40, 45, 50, 55, 60, 65, 70, 75, 80, 85, 88, 90 or 95.

The lipophilic agent of the invention tends to dissolve in other lipophilic substances and/or the agent has little to no capacity to form hydrogen bonds. The terms lipophilicity, hydrophobicity and non-polarity are herein used interchangeably.

Preferably, the lipophilic agent for use in the invention is mostly lipophilic. Alternatively, the therapeutic or diagnostic agent may be only partly lipophilic. Such therapeutic, lubricating or diagnostic agent may be amphiphilic, comprising both hydrophilic and lipophilic properties.

A therapeutic, lubricating or diagnostic agent can be a polymer, a marker, such as a radiopaque dye or particles, or can be a drug, including pharmaceutical agents, or an agent including inorganic, organic or biological drugs without limitation. The agent or drug can be in various forms such as uncharged molecules and components of molecular complexes.

For purposes of illustration and not limitation, the agent can include antithrombotics, anticoagulants, antiplatelet agents, thrombolytics, antiproliferatives, anti-inflammatories, agents that inhibit hyperplasia, inhibitors of smooth muscle proliferation, antibiotics, growth factor inhibitors, or cell adhesion inhibitors. Other agents include but are not limited to antineoplastics, antimitotics, antifibrin, antioxidants, agents that promote endothelial cell recovery, antiallergic substances, radiopaque agents, viral vectors, antisense compounds, cell permeation enhancers, cell adhesion promoters, monoclonal antibodies, hypogylcemic agents, hypolipidemic agents, proteins, agents useful for erythropoiesis stimulation, angiogenesis agents, and combinations thereof.

Examples of lipophilic agents for use in the invention include, but are not limited to at least one of the macrolides, such as cyclosporine (e.g. cyclosporine A (CsA)), rapamycin/sirolimus (RAP or SIR), and FK506/tacrolimus (TAC), or the like, such as everolimus, ridaforolimus, temsirolimus, umirolimus, zotarolimus, ascomycin, FK1012 or pimecrolimus, or structurally related compounds, lutein, alpha-tocopherol, dexamethasone palmitate, Budesonide, Paclitaxel, Ritonavir, Saquinavir, Amprenavir, Valproic acid, Fenofibrate, Bexarotene, Calcitriol, Ibuprofen, Dronabinol, Isotretinoin, Progesterone, Tretinoin, Dutasteride, Doxercalciferol, Carvedilol phosphate, Omega-3-acid ester, Sirolimus, Tolterodine tartrate, Mesalamine, Paricalcitol, NEA, and acylethanolamides such as e.g. PEA (e.g. Agrawal S et al. American J. of Drug Disc. and Develop. 2012; 2(4): 143-183).

Preferably, the lipophilic agent is at least one of an acylethanolamide and a macrolide. Alternatively, the lipophilic agent may be Vitamin K.

In a preferred embodiment, the lipophilic agent for use in the invention is an antibiotic or immunomodulating macrolide. Preferred examples of antibiotic macrolides are Azithromycin, Clarithromycin, Erythromycin, Fidaxomicin, Telithromycin, Carbomycin A, Josamycin, Kitasamycin, Midecamycin, Oleandomycin, Solithromycin, Spiramycin, Troleandomycin, Tylosin and Roxithromycin.

Preferably, the lipophilic agent for use in the invention is an immunomodulating macrolide. In a preferred embodiment, the lipophilic agent is a macrolide selected from the group consisting of cyclosporine, sirolimus, tacrolimus, everolimus, ridaforolimus, temsirolimus, umirolimus, zotarolimus, ascomycin, FK1012 and pimecrolimus. Moreover, the lipophilic agent may be an analog or a derivate (e.g. a structurally related compound) of a lipophilic agent selected from the group consisting of cyclosporine, sirolimus, tacrolimus, everolimus, ridaforolimus, temsirolimus, umirolimus, zotarolimus, ascomycin, FK1012 and pimecrolimus.

In a further preferred embodiment, the lipophilic agent is cyclosporine, sirolimus, or tacrolimus, whereby cyclosporine is the most preferred.

Moreover, a preferred analogue of sirolimus for use in the invention is selected from the group consisting of everolimus, ridaforolimus, temsirolimus, umirolimus and zotarolimus. A preferred analogue of tacrolimus for use in the invention is ascomycin (also called immunomycin, FR900520 or FK520), FK1012 or pimecrolimus It is herein understood that the term Rapamycin/RAP/sirolimus/SIR can be used interchangeable herein. Also, the term tacrolimus/TAC/FK506 can be used interchangeable.

In another preferred embodiment, the lipophilic agent is at least one of an acylethanolamide and a macrolide, such as cyclosporine, rapamycin and tacrolimus. Preferably, the lipophilic agent is a macrolide, and most preferably the lipophilic agent is cyclosporine.

Cyclosporine is a lipophilic agent designed to suppress the immune system. Cyclosporine was the first calcineurin inhibitor available for use, first approved by the FDA in 1983. It is a lipophilic compound that binds to intracellular cyclophilin in T lymphocytes, forming a complex that prevents transcription of interleukin 2, thereby decreasing activation and proliferation of T lymphocytes. It is used in the prevention and treatment of graft-versus-host disease, in bone-marrow transplantation and to prevent rejection of kidney, heart, and liver transplants. It is also approved for the treatment of rheumatoid arthritis and psoriasis, as an ophthalmic emulsion for the treatment of dry eyes and as a treatment for persistent nummular keratitis following adenoviral keratoconjunctivitis. In addition to these indications, cyclosporine is also used in severe atopic dermatitis, Kimura disease, pyoderma gangrenosum, chronic autoimmune urticaria, acute systemic mastocytosis, and, infrequently, in rheumatoid arthritis and related diseases. Furthermore, cyclosporine has also been used to help treat patients with acute severe ulcerative colitis that do not respond to treatment with steroids. This drug is also used as a treatment of posterior or intermediate uveitis with noninfective etiology. Cyclosporine has been used experimentally to treat cardiac hypertrophy. It is sometimes prescribed in veterinary cases, particularly in extreme cases of immune-mediated hemolytic anemia.

The most important effect of cyclosporine is to lower the activity and growth of T cells and their immune response. Treatment with cyclosporine may be associated with a number of potentially serious adverse drug reactions (ADRs). In particular, cyclosporine may be nephrotoxic, neurotoxic, causes hypertension and increases the risk of squamous cell carcinoma and infections. These severe side effects limit the use of this drug for a prolonged and/or systemic treatment.

In a preferred embodiment, the cyclosporine is selected from the group consisting of cyclosporine A (CsA), CsA form 2, cyclosporine B, C, D, E, F, G, H, I, J, K, L, M, N, O, P, Q, R, S, T, U, V, W, X, Y, Z, Voclosporine, Valspodar (PSC833), SCY-635, NIM811 and Debio-025.

Cyclosporine A is highly metabolized in humans and animals after ingestion. The resulting metabolites include cyclosporine B, C, D, E, H, L, and others. Some cyclosporine metabolites have been found to have lower immunosuppressant activity than cyclosporine A and are associated with higher nephrotoxicity. However, for example cyclosporine G (OG37-324), has been found to be less nephrotoxic than cyclosporine A.

In a further preferred embodiment, the cyclosporine is cyclosporine A. Today's marketed formulations of cyclosporine A (CsA) have a number of significant limitations in its use, and so do the competing products in clinical development. These limitations basically all come from a weak formulation strength, which is the collective result of an interconnected sequence of pharmaceutical, pharmacological, toxicological and practical issues. As a consequence, next to limited patient compliance, slow onset of action and low effect rate, and unfavourable safety profile, these formulations are limited in its use.

Alternative names for cyclosporine A may be cyclosporin A, CyA NOF, Neoral, Sandimmune and OL27400 and these names can be used interchangeable herein. Chemically, cyclosporine is designated as [R—[R*,R*-(E)]]-cyclic(L-alanyl-D-alanyl-N-methyl-L-leucyl-N-methyl-L-leucyl-N-methyl-L-valyl-3-hydroxy-N,4-dimethyl-L-2-amino-6-octenoyl-L-α-amino-butyryl-N-methylglycyl-N-methyl-L-leucyl-L-valyl-N-methyl-L-leucyl). The IUPAC name for cyclosporine A is 30-ethyl-33-(1-hydroxy-2-methylhex-4-enyl)-1,4,7,10,12,15,19,25,28-nonamethyl-6,9,18,24-tetrakis(2-methylpropyl)-3,21-di(propan-2-yl)-1,4,7,10,13,16,19,22,25,28,31-undecazacyclotritriacontane-2,5,8,11,14,17,20,23,26,29,32-undecone. Furthermore, Cyclosporine A comprises the molecular formula $C_{62}H_{111}N_{11}O_{12}$ and comprises a molecular structure according the formula (I):

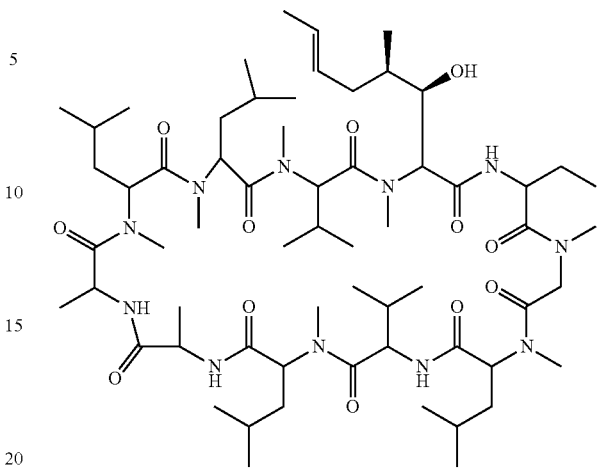

(I)

In an additional or alternative embodiment, the lipophilic agent for use in the invention can be an inhibitor of the mechanistic target of rapamycin (mTOR). Such inhibitors may include the macrolide Sirolimus (Rapamycin) or Ridaforolimus, temsirolimus, or everolimus.

mTOR is also known as mammalian target of rapamycin or FK506-binding protein 12-rapamycin-associated protein 1 (FRAP1). mTOR is a protein that in humans is encoded by the MTOR gene. mTOR is a serine/threonine protein kinase that regulates cell growth, cell proliferation, cell motility, cell survival, protein synthesis, autophagy, transcription. mTOR belongs to the phosphatidylinositol 3-kinase-related kinase protein family, and fibrosis. mTOR inhibitors, e.g. rapamycin, are already used to prevent transplant rejection. Rapamycin is also related to the therapy of glycogen storage disease (GSD). Some articles reported that rapamycin can inhibit mTOR Complex 1 so that the phosphorylation of GS (glycogen synthase) can be increased in skeletal muscle. This discovery represents a potential novel therapeutic approach for glycogen storage diseases that involve glycogen accumulation in muscle. Some mTOR inhibitors (e.g. temsirolimus, everolimus) may also be useful for the treatment of cancer. In addition, mTOR inhibitors may also be useful for treating several age-associated diseases including neurodegenerative diseases such as Alzheimer's Disease and Parkinson's Disease. Ridaforolimus is another mTOR inhibitor, currently in clinical development in cancer.

In yet an additional or alternative embodiment, the lipophilic agent for use in the invention can be an acylethanolamide. Acylethanolamide (NEAs) are lipid-derived signalling molecules. The name acylethanolamine and acylethanolamide may be used interchangeable herein. In a further preferred embodiment the acylethanolamide comprises at least one of palmitoylethanolamide (PEA), oleoylethanolamide (OEA), 2-arachidonylglycerol (2-AG) and anandamide (AEA), or a derivative thereof.

A lipophilic agent for use in the invention can be an acylethanolamide derivative. Examples of such derivates are oleoyl-L-valinolamide, oleoyl-D-valinolamide, elaidoyl-L-valinolamide, elaidoyl-D-valinolamide, stearoyl-L-valinolamide, and palmitoyl-L-valinolamide (Avraham et al, J. Med. Chem (2013) 56(5): 1811-29).

In particular, a lipophilic drug for use in the invention can be a derivative of palmitoylethanolamide, oleoylethanolamide, 2-arachidonylglycerol, anandamide or Stearoylethanolamine. Such derivatives include 2-lineoylglycerol, 2-palmitoylglycerol, JWH-018, JWH-073, CP-55940, Dimethylheptylpyran, HU-210, HU-331, SR144528, WIN 55,212-2, JWH-133, Levonantradol (Nantrodolum), adelmidrol and AM-2201.

In a preferred embodiment, the AEA derivative is selected from the group consisting of JWH-018, JWH-073, CP-55940, Dimethylheptylpyran, HU-210, HU-331, SR144528, WIN 55,212-2, JWH-133, Levonantradol (Nantrodolum), adelmidrol and AM-2201.

A nanoparticle as herein disclosed thus preferably comprises a lipophilic therapeutic or diagnostic agent, wherein the agent preferably is an acylethanolamide and wherein the acylethanolamide comprises at least one of palmitoylethanolamide (PEA), oleoylethanolamide (OEA), 2-arachidonylglycerol (2-AG), anandamide (AEA) and an AEA derivative. The AEA derivative is preferably selected from the group consisting of JWH-018, JWH-073, CP-55940, Dimethylheptylpyran, HU-210, HU-331, SR144528, WIN 55,212-2, JWH-133, Levonantradol (Nantrodolum), adelmidrol and AM-2201.

In a further preferred embodiment of the invention, the lipophilic agent may be palmitoylethanolamide. Palmitoylethanolamide (PEA) is an endogenous fatty acid amide, belonging to the class of nuclear factor agonists. The IUPAC name for PEA is N-(2-hydroxyethyl)hexadecanamide. Other common names for PEA are impulsion, MimyX, N-(2-hydroxyethyl)palmitate, N-palmitoylethanolamine, palmidrol, palmitoylethanolamide and palmitylethanolamide and these names may be used interchangeable herein. The molecular formula is $C_{18}H_{37}NO_2$.

PEA exerts a great variety of biological functions related to chronic pain and inflammation. The main target of PEA is the peroxisome proliferator-activated receptor alpha (PPAR-α). PEA also has affinity to cannabinoid-like G-coupled receptors GPR55 and GRP119 and the presence of PEA has been known to enhance anandamide activity. Its positive influence on chronic pain, and inflammatory states such as atopic eczema, seems to originate mainly from PPAR-α activation.

PEA has been shown to have anti-inflammatory, antinociceptive, neuroprotective and anticonvulsant properties. PEA is currently available for human use as food for medical purposes. Clinical use of PEA is indicated for neuropathic and chronic pain states, such as diabetic neuropathic pain, sciatic pain, CRPS, pelvic pain and entrapment neuropathic pain states.

In another preferred embodiment, the lipophilic agent for use in the invention may be oleoyethanolamide. Oleoylethanolamide (OEA) has anorexic effects and enables fat breakdown by stimulating PPAR-α. It is a naturally occurring ethanolamide lipid that regulates feeding and body weight in vertebrates. OEA is a PPAR-α agonist and can regulate PPAR-α activity to stimulate lipolysis. Moreover, OEA has been demonstrated to bind the cannabinoid receptor GPR119.

In yet another embodiment, the lipophilic agent may be anandamide. Anandamide (AEA) is the ligand of both cannabinoid receptors and vanilloid receptor that attenuates pain sensation. AEA is an endogenous cannabinoid neurotransmitter and AEA effects can occur in either the central or peripheral nervous system. Anandamide plays a role in the regulation of feeding behaviour and the neural generation of motivation and pleasure. Furthermore, anandamide has been proposed as a biomarker of infertility and studies have shown that anandamide can inhibit breast cancer cell proliferation.

The lipophilic agent for use in the invention may be stearoylethanolamine, which has a pro-apoptotic activity. In a preferred embodiment, the acylethanolamide is palmitoylethanolamide (PEA).

A nanoparticle of the invention therefore can be used for the treatment or prevention of a pathology, condition or disorder associated with chronic pain, inflammation, excessive feeding, overweight, obesity, anxiety, depression, Alzheimer's Disease, Parkinson's Disease and/or cancer.

In a preferred nanoparticle according to the invention, the biocompatible lipid may be stabilising and/or lubricating. A stabilising biocompatible lipid is herein understood as the ability of the lipid to contribute to the stability of the nanoparticle. Such stability of the nanoparticle may be assessed using any conventional method known in the art. For example, the stability of a nanoparticle of the invention may be determined by incubating the nanoparticle at about 37° C., e.g. in rat serum, and determining the amount of the lipophilic drug, the biocompatible lipid and/or the water soluble polymer in the composition over time. As a non-limiting example, the biocompatible lipid may confer stability of the nanoparticle when incubated in rat serum, e.g. at about 37° C. Preferably, the addition of the biocompatible lipid to the composition of the nanoparticle results in 1, 10, 20, 50, 75, 80, 90 or 95% less precipitation of the lipophilic drug when incubated for at least 60, 120, 180 or 240 minutes in rat serum at 37° C. as compared to the same nanoparticle without the stabilising biocompatible lipid (and/or having another biocompatible lipid). Preferred stabilizing biocompatible lipids are neutral phospholipids as specified herein below. A particularly preferred stabilizing lipid is HSPC or DSPE, and the most preferred stabilizing biocompatible lipid for use in the invention is HSPC.

Preferably, the biocompatible lipid comprises one or more phospholipids. Phospholipids according to the invention preferably contain a diglyceride, a phosphate group and a simple organic molecule such as choline. In particular, "phospholipids" include phosphatidylcholine (PC), phosphatidylethanolamine (PE), phosphatidic acid (PA), phosphatidylinositol (PI), phosphatidylserine (PS), sphingomyelin, plasmalogens, and phosphatidylcholine lipid derivatives where the two hydrocarbon chains are typically between about 14-22 carbon atoms in length, and have varying degrees of unsaturation.

Alternatively or in addition, the phospholipid may have the following formulae:

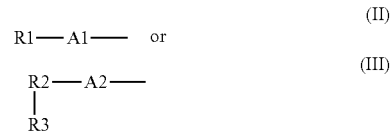

In formula (II), A1 is sphingosine and R1 may comprise octanoyl or palmitoyl. In formula (III), A2 is phosphoethanoamine and R2 and R3 may comprise myristoyl, palmitoyl, stearoyl, or oleoyl, whereby R2 and R3 can be the same or different.

The phospholipid may comprise a net negative electrical charge or a net positive electrical charge. However in a preferred embodiment of the invention, one or more phospholipids are neutral phospholipids. A neutral phospholipid is herein understood as a phospholipid that has no net electrical charge.

In a preferred embodiment of the invention, the biocompatible lipid comprises one or more neutral phospholipids selected from the group consisting of 1,2-dilauroyl-sn-glycero-3-phosphate (DLPA), 1,2-dilauroyl-sn-glycero-3-phosphoethanolamine (DLPE), 1,2-dimyristoyl-sn-glycero-3-phosphate (DMPA), 1,2-dimyristoyl-sn-glycero-3-phosphocholine (DMPC), 1,2-dimyristoyl-sn-glycero-3-phosphoethanolamine (DMPE), 1,2-dimyristoyl-sn-glycero-3-phosphoglycerol (DMPG), 1,2-dimyristoyl-sn-glycero-3-phosphoserine (DMPS), 1,2-dipalmitoyl-sn-glycero-3-phosphate (DPPA), 1,2-dipalmitoyl-sn-glycero-3-phosphocholine (DPPC), 1,2-dipalmitoyl-sn-glycero-3-phosphoethanolamine (DPPE), 1,2-dipalmitoyl-sn-glycero-3-phosphoglycerol (DPPG), 1,2-dipalmitoyl-sn-glycero-3-phosphoserine (DPPS), 1,2-distearoyl-sn-glycero-3-phosphate (DSPA), 1,2-distearoyl-sn-glycero-3-phosphocholine (DSPC), 1,2-distearoyl-sn-glycero-3-phosphoethanolamine (DSPE), 1,2-distearoyl-sn-glycero-3-phosphoglycerol (DSPG), 1,2-distearoyl-sn-glycero-3-phosphoserine (DSPS) and hydrogenated soy phosphatidylcholine (HSPC). In addition, the one or more neutral phospholipids for use in the invention may be soy phosphatidylcholine (SPC) or egg yolk phosphatidylcholine (EYPC). However, SPC and EYPC may be less preferred as lipids for the (solid lipid) nanoparticle of the invention, as these lipids may limit the stability of the nanoparticle, potentially because of the melting point of SPC and EYPC is below room temperature.

According to the invention, the nanoparticle may comprise a single or a variety of biocompatible lipids. In particular, the nanoparticle according to the invention may comprise at least 1, 2, 3, 4, 5, 6, 7, 8, 9 or 10 different biocompatible lipids. Alternatively, the nanoparticle of the invention may comprise at most 1, 2, 3, 4, 5, 6, 7, 8, 9 or 10 different biocompatible lipids.

In a more preferred embodiment, the one or more neutral phospholipids comprise at least one of HSPC and DSPE, and preferably HSPC and DSPE. In a most preferred embodiment, the one or more neutral phospholipids comprise at least HSPC.

The nanoparticle may comprise cholesterol in addition to a phospholipid. Thus in a preferred embodiment, the biocompatible lipid further comprises cholesterol, or a cholesterol derivative. The biocompatible lipid comprises at least about 1, 5, 10, 20, 30, 35, 40 or 45% cholesterol (derivative) (w/w). Preferably, the biocompatible lipid comprises at least 40, 41, 42, 43, 44 or 45% cholesterol (derivative). Alternatively, the molar ratio between a cholesterol (derivative) and a phospholipid is preferably 1:0.3 to 3, more preferably 1:0.5 to 2.5, and most preferably 1:1.0 to 1.5 or around 1:1.3.

Alternatively, in a preferred embodiment, the biocompatible lipid comprises less than 0.1, 0.5, 1, 5, 10, 20, 30, 35, 40 or 45% cholesterol (derivative) (w/w). Preferably, the biocompatible lipid comprises less than 5, 4, 3, 2, 1, 0.5, or 0.1% cholesterol (derivative). In the most preferred embodiment, the nanoparticle does not comprises any cholesterol. It is herein understood that a nanoparticle without cholesterol may encompass nanoparticles having (e.g. undetectable) traces of cholesterol. Most preferably, the amount of cholesterol is low enough to prevent that the nanoparticle forms a liposome.

In a further embodiment of the invention, the water soluble polymer is conjugated to at least one of the biocompatible lipid and the lipophilic therapeutic or diagnostic agent. Preferably, the water soluble polymer is covalently linked to at least one of the biocompatible lipid and the lipophilic therapeutic or diagnostic agent. 'Conjugated to' is herein defined as the coupling of two entities together. Preferably, the two entities are conjugated by non-specific or specific protein-protein interaction, by covalent bonding, by non-covalent bonding, by coordinating chemical bonding and/or by hydrophobic interactions. In the context of the present invention the first entity may be a water soluble polymer as herein defined below, whereas the second entity will be at least one of a biocompatible lipid and the therapeutic or diagnostic agent as defined herein.

In a preferred embodiment, the water soluble polymer as defined below is conjugated to the macrolide (such as cyclosporine) and/or acylethanolamide as defined above, wherein preferably the macrolide is cyclosporine A, tacrolimus or sirolimus. The preferred acylethanolamide is palmitoylethanolamide (PEA). In a more preferred embodiment, the water soluble polymer is conjugated to PEA. In a particularly preferred embodiment PEA is conjugated to polyethylene glycol (PEG) as defined below or a PEG derivative as e.g. disclosed in US2015/0157733. In the most preferred embodiment, PEA is conjugated to 1,2-distearoyl-sn-glycero-3-phosphoethanolamine-N-[methoxy(polyethylene glycol)-2000 (DSPE-mPEG2000).

The water soluble polymer may be a stabilising and/or moisturizing water soluble polymer.

A stabilising water soluble polymer is herein understood as a polymer that contributes to the stability to the nanoparticle e.g. in vivo by increasing the tissue penetration/diffusion depth, the circulation time and/or decreasing bloodstream clearance (so-called "stealth" properties) as compared to the same nanoparticle without the water soluble polymer. The water soluble polymer for use in the invention may alternatively or in addition have a lubricating effect.

In a further embodiment, the nanoparticle comprises a water soluble polymer, wherein the water soluble polymer is at least one of:
 i) a polyalkylether, preferably the polyalkylether is linear polyethylene glycol (PEG), star PEG or multi-arm branched PEG;
 ii) a homopolymer that is a PEG substitute or a PEG alternative, preferably the homopolymer is selected from the group consisting of polymethylethyleneglycol (PMEG), polyhydroxypropyleneglycol (PHPG), polypropyleneglycol (PPG), polymethylpropyleneglycol (PMPG), polyhydroxypropyleneoxide (PHPO), polyoxazoline (POZ) and hydroxyethyl starch (HES);
 iii) a heteropolymer of small alkoxy monomers, preferably the heteropolymer comprises polyethylene/polypropyleneglycol (PEG/PPG).

PEG is also known as polyethylene oxide (PEO) or polyoxyethylene (POE), depending on its molecular weight and these names may be used interchangeable herein. The water soluble polymer may confer stealth-like and/or moisturizing properties to the nanoparticle.

According to the invention, the nanoparticle may comprise a single or a variety of water soluble polymers. In particular, the nanoparticle according to the invention may comprise at least 1, 2, 3, 4, 5, 6, 7, 8, 9 or 10 different water soluble polymers. Alternatively, the nanoparticle of the invention may comprise at most 1, 2, 3, 4, 5, 6, 7, 8, 9 or 10 different water soluble polymers. Furthermore, instead of or in addition to the water soluble polymer as defined herein, the water-soluble polymer may be a derivative of the above-defined polyalkylether, homopolymer and/or heteropolymer. In particular, the water-soluble polymer may be derivatised to comprise carboxylic acid, a maleimide, or an amide for e.g. covalently linking a ligand for targeting.

In a preferred embodiment, the water soluble polymer has a molecular weight of at least about 120 Daltons and up to 20.000 Da. Preferably, the water soluble polymer has a molecular weight between 300 and 50,000 Da, more preferably between 750 and 10,000 Da, and most preferably between 1,000 and 5,000 Da or between 1,000 and 3,400 Da, e.g. around 2000 Da.

In another preferred embodiment, the water soluble polymer has a molecular weight that is less than 20,000, 15,000, 10,000, 5,000, 4,500, 4,000, 3,500, 3,400, 3,300 or 3,200 Da.

In a further preferred embodiment, the water soluble polymer has a polymerization number of at least about 4, 5, 6, 7, 8, 9, 10, 25, 50, 75, 100, 125, 150, 175, 200, 209, 210, 211, 250, 300, 400 or 500. In particular, preferably the water soluble polymer has a polymerization number of at least 6 or about 6-210.

In a further embodiment, the invention relates to a nanoparticle wherein the water soluble polymer is conjugated to the biocompatible lipid. Preferably, the water soluble polymer is covalently linked to the biocompatible lipid.

In a particularly preferred embodiment, the conjugate of the biocompatible lipid and the water soluble polymer is a conjugate of a phospholipid as defined herein, Vitamin E or a derivative of Vitamin E, to a polymer as defined above.

In a preferred embodiment, a phospholipid may be conjugated or linked to a water soluble polymer. Such polymer-phospholipid conjugates may have a stabilising effect on the nanoparticle, and a moisturizing and/or lubricating effect.

When the phospholipid derivatives represented by formula (II) is bonded to PEG or a PEG derivative, it preferably has a molecular weight of about 750-5,500 Da, and when the phospholipid derivatives represented by formula (III) or bonded to PEG or a PEG derivative, it preferably has a molecular weight of about 350-5,500 Da.

In a further preferred embodiment, Vitamin E or a Vitamin E derivative may be conjugated or linked to a water soluble polymer. Preferred Vitamin E derivatives are e.g. described in EP05292820.

More preferably, the conjugate is a 1,2-distearoyl-sn-glycero-3-phosphoethanolamine-N-polyethylene glycol (DSPE-PEG), and most preferably wherein the conjugate is 1,2-distearoyl-sn-glycero-3-phosphoethanolamine-N-[methoxy(polyethylene glycol)-2000] (DSPE-mPEG2000) or d-alpha tocopheryl-N-[methoxy(polyethylene glycol)-1000] (TPEG1000).

In an alternative embodiment of the invention, the conjugate is hydrogenated soy phosphatidylcholine-polyethylene glycol (HSPC-PEG), and most preferably wherein the HSPC-PEG is hydrogenated soy phosphatidylcholine-[methoxy(polyethylene glycol)-2000] (HSPC-mPEG2000).

In an embodiment of the invention, the size of the nanoparticle is between 5-300 nm, preferably the size of the nanoparticle is between 10 and 150 nm and more preferably the size of the nanoparticle is between 20 and 100 nm. The size of the nanoparticle may be determined by any method known in the art. However, preferably the size of the nanoparticle is determined by dynamic light scattering zetasizer.

Preferably, the size of the nanoparticle is at least about 3, 5, 10, 15, 20, 25, 30, 35, 40, 45 or 50 nm and not more than about 350, 300, 250, 200, 175, 150, 125, 100, 75 or 50 nm. More preferably the size of the nanoparticle is about 5, 10, 15, 20, 25, 30, 35, 40, 45, 50, 55, 60, 65, 70, 75, 80, 85, 90, 95 or 100 nm. Most preferably, the size of the nanoparticle is about between 5 and 300 nm, 10 and 150 nm, 15 and 100 nm, 20 and 100 nm, 15 and 80 nm, 20 and 80 nm, 15 and 60 nm or 20 and 60 nm.

In a further preferred embodiment, the invention relates to a composition comprising nanoparticles of the invention, wherein the nanoparticles have an average size of at least about 3, 5, 10, 15, 20, 25, 30, 35, 40, 45 or 50 nm and not more than about 350, 300, 250, 200, 175, 150, 125, 100, 75 or 50 nm. More preferably the average size of the nanoparticles is about 5, 10, 15, 20, 25, 30, 35, 40, 45, 50, 55, 60, 65, 70, 75, 80, 85, 90, 95 or 100 nm. The nanoparticles in the composition may deviate at least 0.01, 0.05, 0.10, 0.15, 0.20, 0.25, 0.30, 0.35, 0.40, 0.45, 0.50, 0.60, 0.70, 0.80, 0.90, 1.0, 2.0 or 5.0 nm from the average size. Most preferably, the size of the nanoparticles in the composition is about between 5 and 300 nm, 10 and 150 nm, 15 and 100 nm, 20 and 100 nm, 15 and 80 nm, 20 and 80 nm, 15 and 60 nm, 20 and 60 nm, 15 and 50 nm, 20 and 50 nm, 15 and 40 nm, 20 and 40 nm, 15 and 30 nm or 20 and 30 nm.

A nanoparticle of the invention can be obtained using any method known in the art. A mixture comprising the nanoparticle may subsequently be sterilized using any conventional method. For example, the mixture comprising nanoparticles of the invention may be sterilized by passing the mixture though a (sterile) filtration filter. Preferably, the filtration filter comprises a pore size of about 0.15, 0.2, 0.25, 0.3, 0.4, 0.5, 0.5 or 1.0 microns.

The invention further relates to a nanoparticle that preferably has a transition temperature above 20 degrees Celsius, more preferably above 30 degrees Celsius and most preferably above 40 degrees Celsius. In an embodiment of the invention, the transition temperature is thus preferably above 20, 25, 30, 37, 40, 45, 50, 55 or 60 degrees Celsius. The transition temperature is herein defined as the temperature where the nanoparticle of the invention loses its distinctive properties. In particular, the transition temperature is herein defined as the temperature wherein the nanoparticle loses the ability to capture the lipophilic agent.

A nanoparticle as disclosed herein may be prepared using any conventional method known in the art. As a non-limiting example, the nanoparticle may be prepared by dissolving a biocompatible lipid, a water-soluble polymer and a diagnostic, lubricating or therapeutic agent in any suitable solvent. Preferred solvents are miscible in water, and are pharmaceutically acceptable. Particularly preferred solvents are ethanol, methanol and isopropanol, more preferably ethanol and methanol. The most preferred solvent is ethanol. The solution may be heated. Preferably, the solution is heated to about 40, 55, 60, 65 or 70 degree Celsius. Subsequently the lipid solution may be added to a suitable aqueous solution, preferably having about the same temperature as the lipid solution. The lipid solution is preferably added slowly, e.g. step-wise. Alternatively, an aqueous solution may be added to the lipid solution. Preferably, the aqueous solution is added slowly, e.g. step-wise. A suitable aqueous solution includes water, saline, phosphate buffered saline, or any other aqueous solution commonly known in the art. A preferred aqueous solution is water. The percentage solvent/aqueous solution is preferably about 5%, 10%, 15%, 20%, 25%, 30%, 35%, 40%, 45%, 50%, 55% or 60% (w/w). After the solution is cooled down, any residual solvent may optionally be removed from the particle solution. Removal of the residual solvent can be done using any conventional method known in the art including, but not limited to, dialysis, diafiltration or liquid chromatography.

In a second aspect, the invention relates to a composition comprising a nanoparticle as defined herein and an excipient or carrier that is suitable for human or veterinary use. In a preferred embodiment, the excipient or carrier is suitable for human use. In particular, the nanoparticle and/or composition of the invention provide for a stable, clear, non-stinging solution, suitable for human and/or veterinary use.

The carrier or excipient can be any compatible, non-toxic substance suitable to administrate the nanoparticle to the subject. Sterile water, alcohol, fats, waxes, and inert solids may be used as the carrier. Pharmaceutically acceptable adjuvants and/or solvents, buffering agents, dispersing agents, stabilizing agents, osmotic agents, and the like, may also be incorporated into the composition.

The concentration of the nanoparticle of the invention in the composition can vary widely, i.e., from less than about 0.1% by weight, usually being at least about 1% by weight to as much as 20% by weight or more.

The excipient or carrier in the composition of the invention may be suitable for human or veterinary use. As used herein, veterinary use concerns the prevention, diagnosis and/or treatment of animals other than humans. In particular, veterinary use covers all animal species, both domesticated and wild. In a preferred embodiment, the excipient or carrier is particularly suitable for use of domesticated animals including, but not limited to, cats, dogs, cattle, goats, horses, donkeys, sheep, domestic rabbits, mice and rats.

The composition preferably comprises at least one excipient or carrier in addition to the nanoparticle. Preferably, the excipient or carrier is a pharmaceutically acceptable excipient or carrier. Hence in a preferred embodiment, the composition is a pharmaceutical composition.

In a further embodiment of the invention, the composition of the invention comprises at least about 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 20%, 30%, 40%, 50% or more (w/w) of the lipophilic therapeutic, lubricating or diagnostic agent. In another embodiment, the composition of the invention comprises at least about 1%-50%, 2%-40%, 3%-30% or 5%-15% (w/w) of the lipophilic therapeutic, lubricating or diagnostic agent, most preferably the composition comprises at least 5%-15% of the lipophilic therapeutic, lubricating or diagnostic agent.

The weight to weight ratio is calculated herein as the percentage of the combined weight of all components used to prepare the nanoparticle. In particular the combined weight includes a biocompatible lipid, a lipophilic agent and a water soluble polymer. Furthermore, the combined weight may include a biocompatible lipid, a lipophilic agent a water soluble polymer and cholesterol. Alternatively, the weight to weight ratio may be calculated herein as the percentage of the weight of the therapeutic, lubricating or diagnostic agent compared to the total weight of the composition.

The ratio of the agent:biocompatible lipid used for preparing the nanoparticle (e.g. the amount dissolved in ethanol or any other suitable solvent) may be around 1:3, 2:3, 3:3, 4:3, 4:3, 1:4, 2:4, 3:4, 4:4, 5:4, 1:5, 2:5, 3:5, 4:5, 5:5, 6:5, more preferably around 1:4, 2:4, 3:4, 4:4, 5:4, and most preferably around 1:4 or 5:4.

In addition, the ratio of the biocompatible lipid:water soluble polymer is preferably around 4:4, 4:5, 4:6, 4:7, 4:8, most preferably the ratio is around 4:6. Hence, the ratio agent:biocompatible lipid:water soluble polymer for preparing the nanoparticle is preferably around 1:4:6, 2:4:6, 3:4:6, 4:4:6 or 4:5:6, of which the ratio around 5:4:6 is most preferred.

In a preferred embodiment, the composition of the invention comprises an effective amount of the diagnostic, lubricating or therapeutic agent. An effective amount is herein defined as an amount sufficient to reduce the severity of symptoms and/or prevent or arrest further development of symptoms and/or lead to a diagnosis after one or multiple administrations. An amount adequate to accomplish this is defined as a "therapeutically-", "prophylactically-" or "diagnostically-" effective dose. Such effective dosages will depend on the severity of the condition and on the general state of the subject's health.

The administration of a clear aqueous solution is known to increase patient compliance. The invention further relates to a composition as defined herein, wherein the composition is a clear aqueous solution, which makes it very distinct from the currently available emulsions. In particular, the composition may be colourless and allows the light to pass through the composition without being scattered. Thus in a preferred embodiment of the invention, the composition is a transparent solution.

A preferred composition of the invention has a turbidity that is not higher than 40, 20, 10, 5, 2 or 1 FTU as determined according to the ISO 7027:1999 standard. Preferably, the turbidity of the composition is not higher than 40, 30, 20, 15, 10, 9, 8, 7, 6, 5, 4, 3, 2, 1, 0.9, 0.8, 0.7, 0.6, 0.5, 0.4, 0.3, 0.2 or 0.1 FTU according to the ISO 7027:1999 standard.

FTU (Formazin Turbidity Unit), FNU (Formazin Nephelometric Units) and NTU (Nephelometric Turbidity Unit) can be used interchangeable herein. In an alternative embodiment, the turbidity is not higher than 40, 20, 10, 5, 2 or 1 FNU as determined according to the ISO 7027:1999 standard. In particular, the turbidity of the composition is not higher than 40, 30, 20, 15, 10, 9, 8, 7, 6, 5, 4, 3, 2, 1, 0.9, 0.8, 0.7, 0.6, 0.5, 0.4, 0.3, 0.2 or 0.1 FNU according to the ISO 7027:1999 standard. In a further alternative embodiment, the turbidity of the composition is not higher than 40, 20, 10, 5, 2 or 1 NTU as determined according to EPA method 180.1. In particular, the turbidity is not higher than 40, 30, 20, 15, 10, 9, 8, 7, 6, 5, 4, 3, 2, 1, 0.9, 0.8, 0.7, 0.6, 0.5, 0.4, 0.3, 0.2 or 0.1 NTU according to the EPA method 180.1.

In particular, the composition may comprise a percentage of the lipophilic therapeutic, lubricating or diagnostic agent as defined above and is a clear aqueous solution as defined above. Thus in a preferred embodiment, the composition is a clear aqueous solution comprising at least 0.05%, 0.1%, 0.5%, 1%, 5% or 10% (w/w) of the lipophilic therapeutic, lubricating or diagnostic agent.

A composition as described herein may be a hypertonic, hypotonic or isotonic composition. Preferably, the composition is an isotonic composition. In a further preferred embodiment, the isotonic composition comprises a tonicity that is equal to that of an about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 or 2.5% solution of sodium chloride (w/v). Preferably, the isotonic composition comprises a tonicity that is equal to that of a 0.7-1.1% solution of sodium chloride, and more preferably the isotonic composition comprises a tonicity that is equal to that of an about 0.9% solution of sodium chloride.

In another preferred embodiment, the composition comprises a pH between pH 4.0-10.0, preferably the pH is between pH 5.0-9.0, pH 6.0-8.0, pH 6.5-7.5 or pH 7.0-8.0. Preferably, the pH of the composition is about 4.0, 5.0, 6.0, 6.5, 7.0, 7.2, 7.3, 7.4, 7.5, 7.6, 7.7, 8.0, 8.5, 9.0 or 10.0, most preferably the pH is about 7.4.

In a further embodiment, the composition as defined herein is in a formulation selected from the group consisting of a cream, an ointment, a gel, a solution for spray delivery, an eyewash, a liniment, a patch, a lotion, a wipe, a pad, a towelette, an eye wipe, an eye drop, an ear drop, a solid dosage form, a capsule, a tablet, (freeze-dried) powders or tablet, a dry powder, an aerosolic dosage form for inhalation, nebulisation or nasal delivery, a liquid dosage form, an elixir, a syrup, and an intravenous infusion fluid. Preferred formulations are a spray, an eye drop or an intravenous infusion fluid. The spray formulation may be for a topical or local application, e.g. for application to the eye, skin surrounding the eye or mouth.

In particular, the formulation may be in solid dosage forms, such as capsules, tablets, and powders, or in liquid dosage forms, such as elixirs, syrups, and suspensions. The nanoparticle can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable colour, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract.

Liquid dosage forms can contain colouring and flavouring to increase patient acceptance. Compositions and/or formulations comprising the nanoparticle are preferably sterile. Sterilisation is readily accomplished by filtration through sterile filtration membranes, prior to or following lyophilisation and reconstitution. A typical formulation for intravenous infusion could be made up to contain 10 to 500 ml of sterile 0.9% NaCl (w/v) or 5% glucose (w/v) optionally supplemented with a 20% albumin solution (w/v) and the required dose of the nanoparticle. A typical formulation for intramuscular injection would be made up to contain, for example, 1-10 ml of sterile buffered water and the required dose of the nanoparticle of the invention. Methods for preparing parenterally administrable formulations are well known in the art and described in more detail in various sources, including, for example, "Remington: The Science and Practice of Pharmacy" (Ed. Allen, L. V. 22nd edition, 2012, www.pharmpress.com) (incorporated by reference in its entirety for all purposes). The nanoparticle or composition may be administered continuously by infusion or by bolus injection.

In a particular preferred embodiment, a nanoparticle or a composition as defined herein may be in an eye drop formulation as defined below. Such eye drop formulation may effectively deliver (lipophilic) agents to the choriocapillaris behind the eye, the heart, the lung, the coronary vasculature of the heart, the aorta, the cerebrovasculature, brain and eye, and/or the systemic circulation.

In another embodiment of the invention the composition comprises at least one further diagnostic or therapeutic agent. The further diagnostic or therapeutic agent may complement the lipophilic agent or may be synergistic. In particular, the composition may further comprise 1-theanine, vitamin D, glucosamine, Boswellia serrate extracts, vanadium salts such as bis (maltolato)oxovanadium and/or picamilon. These compounds are classified as supplements, and their mechanism of action may work synergistically to that of a macrolide and/or an acylethanolamide, such as palmitoylethanolamide.

Alternatively or in addition, the composition as defined herein may further comprise a substrate for a drug efflux pump. Preferably, the composition further comprises at least one effective amount of a substrate for a drug efflux pump. The substrate for a drug efflux pump may be a substrate for P-glycoprotein (Pgp), multidrug resistance protein (MRP-1), breast cancer resistance protein (BCRP), and lung resistance protein (LRP). The substrate may also be a substrate of another drug efflux pump.

The substrate for a drug efflux pump may be a kinase inhibitor selected from the group consisting of ABT-869, afatinib (BIBW-2992), AMG-706, AMN-107, amuvatinib, AST-487, axitinib (AG-013736), AZD-152HQPA, AZD-2171, BIBF-1120, BIRB-796, BMS-540215, bosutinib, cabozantinib, canertinib (C1-1 033), CHIR-258/TKI-258, crizotinib, dasatinib, DMBI, dovitinib, erlotinib, everolimus, EXEL-2880/GSK-1363089, gefitinib, GW-786034, imatinib, JNJ-28312141, Ki-20227, Ki8751, lapatinib, masitinib (AB-1 01 0), midostaurin (PKC-412), motesanib, neratinib (HKI-272), nilotinib, OSI-930, pazopanib, PD-173955, PLX-4720, ponatinib, PTK-787, quizartinib (AC220), R406, regorafenib, SKI-606, sorafenib, staurosporine, SU-14813, sunitinib, tandutinib (MLN-518), telatinib, temsirolimus, tivozanib, vandetanib, vatalanib, and vemurafenib.

Alternatively, the substrate for a drug efflux pump may be selected from the group consisting of darunavir, maraviroc, digoxin, loperamide, quinidine, vinca alkaloids (e.g., vinblastine or vincristine), acrivastine, talinolol, ketoconazole, zosuquidar (LY335979), nelfinavir, ritonavir, saquinavir, tacrolimus, valspodar, verapamil, elacridar, reserpine, amiodarone, azithromycin, captopril, carvedilol, clarithromycin, conivaptan, diltiazem, dronedarone, dexamethasone, betamethasone, erythromycin, felodipine, itraconazole, lopinavir, quercetin, ranolazine, aliskiren, ambrisentan, colchicine, dabigatran etexilate, everolimus, fexofenadine, imitanib, lapatinib, nilotinib, posaconazole, saxagliptin, sirolimus, sitagliptin, tolvaptan, topotecan, indinavir, an anthracycline, doxorubicin, duanorubicin, epirubicin, mitxantrone, etoposide, amprenavir, ranitidine, propanalol, prazosin, methotrexate, cefazolin, cefoperazone, cerivastatin, cetirizine and mitomycin C.

Alternatively or in combination with any of the embodiments above, the substrate for a drug efflux pump may be a substrate selected from the group consisting of the class of taxanes (e.g., paclitaxel or docetaxel), antiviral drugs, anti-allergy drugs, anti-bacterial drugs, anti-infective drugs, anti-glaucoma drugs (such as β-adrenergic blocking agents, carbonic anhydrase inhibitors, miotic, sympathomimetic and prostaglandin agonists), anti-inflammatory drugs (such as methylprednisolone or dexamethasone), anti-angiogenesis drugs (such as kinase inhibitors), neuroprotective drugs, nerveprotective drugs and drugs that protect photoreceptors.

In a third aspect, the invention relates to a nanoparticle as defined herein or a composition as defined herein for use as a medicament.

In a fourth aspect the invention pertains to a nanoparticle as defined herein or a composition as defined herein for use in the prevention or treatment of a pathology, condition or disorder associated with:
  a) pain;
  b) disruption of an epithelial or endothelial barrier;
  c) decreased blood pressure;
  d) decreased local vascular blood flow;

e) decreased clearance from cellular waste materials;
f) mitochondria dysfunction;
g) activation of the immune system;
h) inflammation;
i) decreased ocular humor outflow and/or other ocular diseases;
j) cancer;
k) neuronal disorder; or
l) organ rejection;
m) viral diseases;
n) trauma, surgery and wound healing;
o) genetic diseases;
p) infectious diseases; and/or
q) eye diseases.

In a preferred embodiment, the invention relates to a nanoparticle or composition for use as a medicament as defined herein, wherein the medicament may be used for the prevention or treatment of a pathology, condition or disorder as defined above.

A particularly preferred nanoparticle or composition of the invention is a nanoparticle or composition wherein the agent is a macrolide and the nanoparticle or composition is for use in the prevention or treatment of a pathology, condition or disorder as specified herein.

A particularly preferred pathology or disorders is associated with inflammation, impaired vascular blood flow, cancer and/or neuronal disorders.

The nanoparticles of the invention may further be used for the treatment or prevention of a pathology or condition associated with the dermis or mucosa, particularly psoriasis, atopic dermatitis or eczema, oral lichen planus and/or geographic tongue/migratory glossitis. In an embodiment of the invention, the nanoparticle as disclosed herein may be used for the prevention or treatment of an inflammatory disorder, degenerative disorder, viral infection, genetic disease, environmental disease, pain, proliferative disease, metabolic disease and/or ischaemic disease.

In a further preferred embodiment of the invention, the nanoparticle as disclosed herein can be used for the prevention or treatment of a pathology, condition or disorder associated with peripheral, ocular and/or central diseases, and/or pain. Preferably, the cause of the pain is selected from a group consisting of: inflammation, neuroinflammation, non-infectious trauma, wound healing, surgery, allergies, auto-immunity, organ or cell rejection after transplantation, epithelial barrier dysfunction, macro- and/or microvascular dysfunction, impaired blood flow, reperfusion damage, environmental origins, infectious origins and genetic origins.

In another preferred embodiment, the invention relates to a nanoparticle or composition for use in moisturizing tissues, lubricating tissues, modulation or inhibition of drug efflux pumps, improving or repairing epithelial barrier properties, improving or repairing endothelial barrier properties, increasing blood pressure, improving local vascular blood flow, improving clearance from cellular waste materials, treating or prevention of mitochondria dysfunction, a suppressing the immune system, preventing or silencing inflammation, inducing anti-nociceptive effects, inducing analgesic effects, increasing ocular humor outflow, exhibiting neuroprotective effects, exhibiting anti-cancer effects, inducing anti-convulsive effects and/or anti-epileptic effects.

In a further embodiment, the invention pertains to a nanoparticle or composition as defined herein for use in the prevention or treatment of a pathology, condition or disorder associated with a trauma, such as a surgical trauma. Preferably, the trauma leads to a disruption and/or breakdown of a natural cellular barrier. More preferably, the nanoparticle or composition of the invention may be used in the prevention or treatment of a pathology, condition or disorder associated with the disruption or breakdown of an endothelial and/or epithelial barrier. The endothelial or epithelial barrier may be selected from the group consisting of the blood-brain barrier, blood-CSF barrier, blood-ependyma barrier, blood-spinal cord barrier, blood-nerve barrier, blood-retina barrier, blood-testes barrier, blood-placenta barrier, corneal epithelium barrier, retinal pigment epithelium barrier, blood-inner ear barrier, blood-labyrinth barrier, kidney tubular epithelium barrier, intestinal epithelium barrier and skin epithelium barrier.

The disruption or breakdown of the endothelial and/or epithelial barrier may cause or sustain peripheral, ocular and/or central diseases. In a preferred embodiment of the invention, the nanoparticle or composition may be therefore used for the prevention and/or treatment of Alzheimer's Disease, Parkinson's Disease, pain, and/or loss in tissue homeostasis. In a preferred embodiment, the treatment is effectively improving or repairing such disrupted epithelial or endothelial barrier properties.

To exert these specific effects, the lipophilic agent for use in the invention may be acting on cyclophilins, such as cyclophilin A (CypA), thereby resulting in the normalization of barrier integrity through inhibition of the CypA-NF-kB-MMP9 pathway. Alternatively, the lipophilic agent for use in the invention may be acting on modulation of tight junction proteins (such as occludin, claudins (1, 4, 5) and/or ZO-1,2), thereby resulting in the decrease of paracellular permeability and normalization or improvement of barrier integrity, such as through modulation of the ERK1/2 MAPK signalling pathways and/or increased production and secretion of TGF-beta and expression of the TGF-beta receptor II.

In yet another embodiment, the nanoparticle and/or composition as defined herein may be used to increase blood pressure, improve local vascular blood flow and/or improve clearance from cellular waste materials. The increase in blood pressure, improvement in local vascular blood flow and/or improvement in clearance from cellular waste material may be increased or improved towards a reference value known in the art. Preferably, the reference value is based on a healthy subject or healthy subjects, e.g. the healthy subject or healthy subjects are not in need of treatment to increase blood pressure, improve local vascular blood flow and/or improve clearance from cellular waste materials.

In a further preferred embodiment, the clearance from cellular waste materials concerns the clearance of lipid or protein aggregates. Preferably, the clearance of cellular waste material occurs through stimulation of the renin—angiotensin system, sympathetic activation, endothelin release nitric oxide production, and/or production of reactive oxygen species. Preferably, the clearance of cellular waste material is induced by elevated angiotensin II levels.

In a preferred embodiment of the invention, the nanoparticle or composition as defined herein can be used for the prevention or treatment of dry AMD. In dry AMD the cellular waste material that is depositing as so-called "drusen" is leading to geographic atrophy (GA). Drusen is lipid waste material from the rods and cones and is build up due to a poor vascular flow in the area.

In a preferred embodiment, the nanoparticle or composition as defined herein may comprise a lipophilic agent that inhibits, mTOR, calcineurin and/or cyclophilin. Hence, the nanoparticle or composition of the invention may be used for the prevention or treatment of a pathology, condition or disorder associated with impaired blood flow, organ perfusion and/or mitochondrial dysfunction. In particular, the nanoparticle or composition as defined herein may be used for the prevention or treatment of neurodegenerative disorders, (diabetic) ischemic/reperfusion diseases of the heart, lung, kidney, liver, brain, eye, and/or viral diseases.

Particularly preferred neurodegenerative disorders for treatment with a nanoparticle or composition of the invention are Alzheimer's Disease, Parkinson's Disease, Huntington's Disease, multiple sclerosis, amyotrophic lateral sclerosis, stroke, traumatic brain injury and/or spinal cord injury. Particularly preferred (diabetic) ischemic/reperfusion diseases are retinal vein occlusion, diabetic retinopathy, retinopathy of prematurity, dry and wet age related macular degeneration, geographic atrophy. Particularly preferred viral diseases for treatment with a nanoparticle or composition of the invention include hepatitis B, hepatitis C and/or HIV.

In a further preferred embodiment, the lipophilic agent for use in the invention may inhibit calcineurin and/or inducible nitric oxide synthase (iNOS), thereby effectively modulating inflammatory cytokine (receptor) expression levels, such as for interleukin-2, interleukin-4 and/or interleukin-2 receptor (thereby reducing T-cell levels and/or proliferation) and tumor necrosis factor alpha leading to an effective suppression of the immune system. Therefore, a nanoparticle or composition according to the invention may be used for the prevention or treatment of immune system related conditions or disorders, preferably the pathology, condition or disorder is associated with an activation of the immune system. Particularly preferred immune system related conditions or disorders that may be treated with a nanoparticle or composition as defined herein are multiple sclerosis, uveitis, optic neuritis, Behçet's Disease, Vogt-Koyanagi-Harada (VKH) syndrome, Graves' ophthalmopathy, vernal keratino-conjunctivitis (VKC), blepharitis, conjunctivitis, keratitis (dry eye), (epi)scleritis, meibomitis, pterygium, allergy, auto-immunity, irritation, hypersensitivity, wound healing from trauma or surgery, organ or cell rejection after transplantation, inflammatory pain, arthritis, arthrosis, osteoarthritis, rheumatoid arthritis, Crohn's disease, inflammatory bowel disease, psoriasis, asthma, atherosclerosis, peritonitis, pericarditis, dermatitis, urticaria, angioedema, systemic lupus erythematosus (SLE), and/or viral diseases as defined above. In addition, the nanoparticle or composition of the invention may be used for improving gene therapy, enzyme replacement therapy, or for the improvement of any other therapy with biologics. Preferably, the nanoparticle or composition of the invention improves the therapy by preventing neutralizing antibody formation. An improvement in therapy is herein defined as an improvement in the therapeutic effect of the therapy when the therapy is given in combination with a nanoparticle or composition of the invention, as compared to the therapy given without a nanoparticle or composition of the invention.

In a further preferred embodiment, the lipophilic agent for use in the invention may activate specific membrane or nuclear receptors, including but not limited to, peroxisome proliferator-activated receptor alpha (PPAR-α), central (CB1) and peripheral (CB2) cannabinoid receptors, cannabinoid-like G protein-coupled receptors (GPR55 and GPR119) and/or transient receptor potential cation channel subfamily V member 1 (TRPV1). Therefore in another embodiment of the invention, the nanoparticle or composition of the invention may be used for the treatment or prevention of a pathology, condition or disorder associated with chronic pain, neuropathic pain, viral pain, (neuro)inflammation, intra-ocular pressure, intestinal motility and secretion, and/or cellular proliferation. Treatment with a nanoparticle of composition of the invention may result in analgesic, anti-nociceptive, anti-inflammatory, anti-convulsant, anti-epileptic, neuroprotective, anti-cancer, anti-fibrotic, and/or aqueous humor outflow stimulating effects. The stimulation of aqueous humor outflow by the nanoparticle or composition of the invention is important as treatment for glaucoma.

In a preferred embodiment, the nanoparticle or composition of the invention may be used in the prevention or treatment of a pathology, condition or disorder associated with an eye disease. In particular, the nanoparticle of the invention may be used for an ophthalmological treatment. Preferably, the nanoparticle or composition of the invention may be used for the treatment of a pathology, condition or disorder selected from the group of: age-related macular degeneration, bulging eyes (proptosis), cataracts (including or especially cataracts in babies), CMV retinitis, color blindness, crossed eyes (strabismus), diabetic macular edema, eye floaters and eye flashes, glaucoma, keratoconus, lazy eye, low vision, ocular hypertension, retinal detachment, eyelid twitching, uveitis (including or especially auto-immune uveitis), dry eyes, dry eye syndrome, irritated eyes, corneal graft rejection, posterior blepharitis, atopic kerato-conjunctivitis, vernal keratoconjunctivitis, seasonal allergic conjunctivitis, perennial allergic conjunctivitis and herpetic stromal keratitis.

Compositions comprising the nanoparticle of the invention have been found to be quickly soothing and relaxing to the irritated, injured or inflamed eye, mucosal tissue, wound, or surrounding tissues when administered in an eye drop or spray formulation. Likewise, a composition comprising the nanoparticle of the invention is surprisingly found to be non-stinging, non-burning, non-irritating to mucosal tissue, wound, or surrounding tissue when administered in a therapeutically effective formulation, as well as to be non-stinging, or non-burning, non-allergic, non-anaphylactic and non-immunogenic when administered in a therapeutically effective intravenous infusion regimen.

In a further embodiment, the invention relates to a nanoparticle for use in an ophthalmological treatment as defined above, wherein the nanoparticle comprises a biocompatible lipid and a water soluble polymer. In addition, the invention pertains to a nanoparticle for use in a nasal, oral, mucosal or dermal treatment as defined above, wherein the nanoparticle comprises a biocompatible lipid and a water soluble polymer.

In a preferred embodiment, the biocompatible lipid is a lipid as defined above. In addition or alternatively, the water soluble polymer is a polymer as defined above. The nanoparticle may further comprise a lipophilic agent as defined above.

In a preferred embodiment, the ophthalmological treatment comprises the treatment or prevention of at least one of dry, injured and irritated eyes.

Injured eyes are herein to be understood as unintended and/or intended injuries to the eyes. Non-limiting examples of intended injuries to the eyes are for example incisions made for a lens replacement, laser-assisted in situ keratomileusis (LASIK), etc.

In particular, a nanoparticle, composition or formulation of the invention can also be used as smoothening moisturizer and lubricant. Dry eyes may occur when tears are not able to provide adequate moisture for the eye or eyes. Furthermore, dry eyes may occur if not enough tears or poor-quality tears are produced. Dry eyes may occur due to environmental factors, such as e.g. dry air in an airplane or in an air-conditioned room. Alternatively or in addition, dry eyes may occur due to behaviour, such as staring at a computer screen. Dry eyes can be a transient or chronic condition. Dry eyes as defined herein also includes dry eye syndrome (DES, also called Keratoconjunctivitis sicca (KCS), or keratitis sicca). Dry eye syndrome is caused by a chronic lack of sufficient lubrication and moisture on the surface of the eye or eyes. Its consequences range from subtle but constant irritation to inflammation of the anterior tissues of the eye or eyes. Keratoconjunctivitis sicca refers to eye dryness affecting both the cornea and the conjunctiva. Persistent dryness, scratchiness, red eyes and a burning sensation are common symptoms of dry eyes.

Irritated eyes can have many causes, including but not limited to, infection, inflammation, allergy, broken blood vessels and trauma. Preferably, irritation of the eye includes at least one of redness, itching, swelling, burning, trauma, pain, blur and spots, flashes and floaters.

In a fifth aspect, the invention relates to a method for treating or preventing any of the above pathologies, conditions or disorders by administration of a therapeutically or prophylactically effective amount of (a pharmaceutical composition comprising) a nanoparticle of the invention, to a subject in need of prophylaxis or therapy.

In another aspect, the invention pertains to a nanoparticle or composition as defined herein for use in the prevention or treatment of a pathology, condition or disorder, wherein nanoparticle or the composition is administered by at least one of intravenous, intraperitoneal, intramuscular, intraarterial, intralesional, intracranial, intraocular, conjunctival, intracorneal, ophthalmic, dermal, mucosal, nasal or oral routes, wherein preferably the treatment comprises administrating by intraocular, dermal, mucosal, conjunctival or ophthalmic routes. Most preferably, the nanoparticle or composition is administered by an ophthalmic route.

In a preferred embodiment the nanoparticle or composition is administered for the prevention or treatment of a pathology, condition or disorder as defined above. Preferably, the pathology, condition or disorder is selected from the group consisting of: pain, disruption of an epithelial or endothelial barrier, decreased blood pressure, decreased local vascular blood flow, decreased clearance from cellular waste materials, mitochondria dysfunction, activation of the immune system, inflammation, decreased ocular humor outflow and/or other ocular diseases, cancer, neuronal disorder, organ rejection, viral diseases, trauma, surgery, wound healing, genetic diseases, infectious diseases and eye diseases.

In a preferred embodiment, the medicament is administrated to a subject by at least one of intravenous, intraperitoneal, intramuscular, intraarterial, intralesional, intracranial, conjunctival, intracorneal, ophthalmic, intrathecal, intraocular, suprachoroidal, intracerebroventricular, subdural, epidural, intratympanic, intraarticular, transdermal, dermal, intraoral, oral, nasal, buccal, sublingual, rectal, or vaginal routes.

A preferred systemic administration of a nanoparticle or a composition as defined herein is by injection or infusion by at least one of intravenous, intraperitoneal and intraarterial routes.

A preferred topical ocular administration of a nanoparticle or a composition as defined herein is at least one of ophthalmic, intraocular and conjunctival routes. In case part of the eye or eyes is covered, for example by a contact lens, topical ocular administration of a nanoparticle of a composition as defined herein may or may not require the removal of such contact lens.

Preferably for parenteral administration, the (composition comprising) nanoparticle should be sterile. For topical administration, such as ocular administration, the (composition comprising the) nanoparticle may or may not be sterile.

The nanoparticle of the invention has inert (stealth-like) and stable properties. This nanoparticle enhances the delivery of at least one (lipophilic) agent in particular tissues of the body, likely by means of passive targeting based on the enhanced permeability and retention (EPR) effect. In a preferred embodiment, the nanoparticles can enhance the delivery of a lipophilic drug towards:
 a) organs of the reticuloendothelial system, especially or including the liver and/or the spleen;
 b) tissues with leaky tumor and/or inflammatory vasculature;
 c) the skin;
 d) organs with a choroidal vascular bed, especially or including the choriocapillaris behind the eye and/or the choroid plexus in the central nervous system.

Preferably, this distribution pattern is found after topical and/or systemic administration, either enteric or parenteral, both after acute and chronic administration, either as bolus or as continuous administration.

In a particular embodiment, the delivery of the lipophilic agent is enhanced as compared to the delivery of the same lipophilic agent when it is not present in the nanoparticle of the invention. Preferably, the delivery is 1%, 2%, 3%, 5%, 10%, 15%, 20%, 30%, 40%, 50%, 60%, 70%, 80%, 90%, 100%, 125%, 150%, 175%, 200%, 300% or 400% enhanced as compared to the delivery of a lipophilic agent that is not present in a nanoparticle of the invention, e.g. a "naked" lipophilic drug.

In a further embodiment, the invention pertains to a nanoparticle or a composition for a use as defined herein, wherein the administration of the nanoparticle or composition is in separate, combined or sequential administration with the substrate for of a drug efflux pump.

A sequential administration is herein defined as the administration of the nanoparticle or composition prior to the administration of the substrate for a drug efflux pump. Alternatively, sequential administration is herein defined as the administration of the substrate for a drug efflux pump prior to the administration of the nanoparticle or composition. Sequential administration is herein further defined that there is less than 1, 2, 3, 4, 5, 6, 7, 8, 9, 10, 20, 30, 40, 50, or 60 minute(s) apart between the administration of the nanoparticle/composition and the administration of the substrate for the drug efflux pump. In particular, if there is more than 10, 20, 30, 40, 50, or 60 minute(s) apart between the administration of the nanoparticle or composition and the administration of the substrate for a drug efflux pump, it is herein defined that the administration of the nanoparticle/composition and the substrate for the drug efflux pump is separate. In addition if there is less than 1, 2, 3, 4, 5, 6, 7, 8, 9, 10 minutes apart between the administration of the of the nanoparticle or composition and the administration of the substrate for a drug efflux pump, it is herein defined that the administration of the nanoparticle/composition and the substrate for the drug efflux pump is a combined administration.

The nanoparticle or composition as disclosed herein may be administrated daily at least once, twice, three, four, five, six or more times. In addition, the substrate for the efflux pump may be administrated daily at least once, twice, three, four, five, six or more times. The nanoparticle or composition of the invention may be administrated daily as often, less often or more often than the daily administration of a substrate for a drug efflux pump. As a non-limiting example, the nanoparticle or composition comprising the nanoparticle may be administrated twice a day and the substrate for the drug efflux pump may be administrated once a day, or vice versa. The nanoparticle or composition as disclosed herein and/or the substrate for a drug efflux pump may be administrated once every two, three, four or five days or less often.

In a further aspect, the invention pertains to an eye drop formulation, comprising a nanoparticle, a composition or formulation as defined above. Eye drop formulations are known in the art, and any eye drop formulation may be suitable for use in the invention. Eye drop formulations preferably are saline-containing drops which may or may not contain an therapeutic agent. Eye drops sometimes are only lubricating and can be used as tear-replacing solutions. Therefore, the eye drop formulation may comprise a nanoparticle as defined herein, wherein the nanoparticle does not comprise a lipophilic agent. In an alternative embodiment, the nanoparticle may comprise a diagnostic or therapeutic lipophilic agent.

An eye drop formulation of the invention may comprise a preservative in addition to the nanoparticle, composition or formulation as defined above. Preferably, the preservative is a detergent preservative, an oxidizing preservative and/or an ionic-buffered preservative. More preferably, the preservative may be selected from the group consisting of: Benzalkonium chloride, Sodium chlorate, phenoxyethanol, Polexitonium, GenAqua, Chlorobutanol, TBA, Purite, silver sulphate, Polyhexamethylene Biguanide, Butylated hydroxyanisole, Polyquaternium-1 (Polyquad) and Sodium perborate. Alternatively, the eye drop formulation of the invention does not comprise a preservative, as preservatives may irritate the eye.

An eye drop formulation may comprise at least one further ingredient. This further ingredient may be selected from the group consisting of: antihistamines, mast cell stabilizers, decongestants, (nonsteroidal) anti-inflammatory drugs, corticosteroids, benzalkonium chloride, boric acid, borax, disodium EDTA, sodium borate, zinc sulphate, calcium chloride, magnesium chloride, phosphonic acid, sorbitol, potassium chloride, sodium hydroxide, sodium chloride, carboxymethylcellulose sodium, hydroxyethyl cellulose, hydroxypropyl methylcellulose, methylcellulose, trehalose, hypromellose, polyacrylic acid (carbomer), hyaluronan, dextran, gelatin, glycerine, polyethylene glycol, polysorbate 80, polyvinyl alcohol, povidone, taurine and (purified) water. Preferred ingredients are selected form the group consisting of trehalose, hypromellose, sodium chloride, boric acid and borate. In particular, further ingredients may be added to the eye drop formulation to adjust the viscosity and/or the osmolarity and/or the pH of the eye drop formulation. As non-limiting examples, a preferred ingredient to adjust the viscosity is hypromellose, a preferred ingredient to adjust the osmolarity is trehalose and/or sodium chloride and a preferred ingredient to adjust the pH is boric acid.

Preferably, the eye drop formulation comprises at least 1, 2, 3, 4, 5, 6, 7, 8, 9 or 10 further ingredients.

An eye drop formulation as described herein may be an hypertonic, hypotonic or an isotonic formulation. Preferably, the eye drop formulation is an isotonic formulation. In a further preferred embodiment, the isotonic eye drop formulation comprises a tonicity that is equal to that of an about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 or 2.5% solution of sodium chloride (w/v). Preferably, the isotonic eye drop formulation comprises a tonicity that is equal to that of a 0.7-1.1% solution of sodium chloride, and more preferably the isotonic formulation comprises a tonicity that is equal to that of an about 0.9% solution of sodium chloride.

In another preferred embodiment, the eye drop formulation comprises a pH between pH 4.0-10.0, preferably the pH is between pH 5.0-9.0, pH 6.0-8.0, pH 6.5 7.5 or pH 7.0-8.0. Preferably, the pH of the eye drop formulation is about 4, 5, 6, 6.5, 7, 7.2, 7.3, 7.4, 7.5, 7.6, 7.7, 8, 8.5, 9 or 10, most preferably the pH is about 7.4.

Preferably, the eye drop formulation is a sterile formulation.

In another aspect, the invention relates to an applicator for applying an effective amount of an eye drop formulation to an eye, wherein the applicator comprises the eye drop formulation as described above. Applicators for eye drops are commonly known in the art and any applicator for applying an eye drop formulation can be used for applying an eye drop formulation of the invention. Preferably, the eye drop applicator is a bottle for administering a liquid eye drop. More preferably, the eye drop applicator comprises a container for holding the eye drop formulation as described herein, a dispensing assembly and a closure assembly. The dispensing assembly may comprise a passage for dispensing the liquid eye drop from the container, e.g. a tapered dropper. Alternatively, the eye drop applicator may vaporize the eye drop formulation. The eye drop applicator may be disposable eye drop applicator, e.g. may be used only once, or may be reusable. Furthermore, the invention pertains to an applicator comprising the nanoparticle, composition or formulation as defined herein, wherein the applicator can be used to apply an effective amount to the (sensitive) skin around the eye, scalp, skin lesions, nasal cavity and/or mouth. Preferably, the applicator can topically spray the nanoparticle, composition or formulation as defined herein onto the affected area.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

Figure 1:
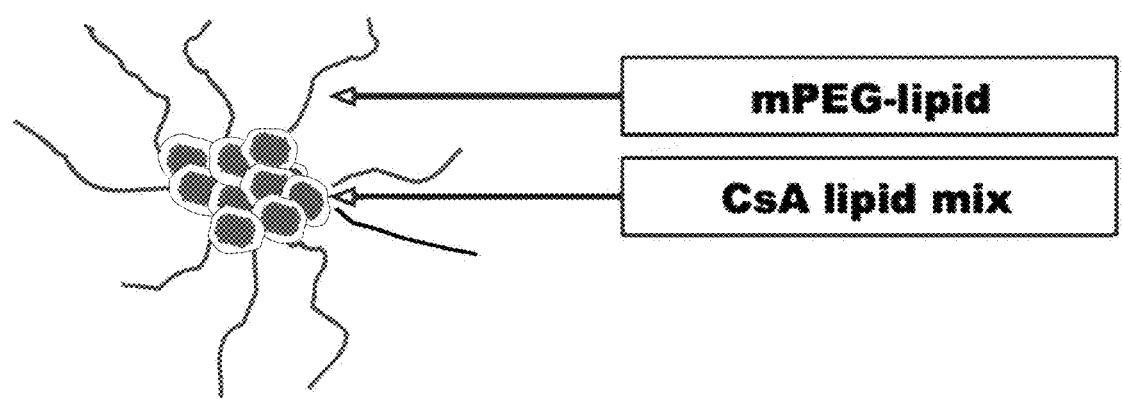
FIG. 1. Schematic drawing of a nanoparticle according to the invention, wherein the nanoparticle comprises the lipophilic agent CsA, at least two biocompatible lipids, wherein at least one biocompatible lipid is conjugated to the water soluble polymer PEG.

Example 1. Preparation of a Nanoparticle According to the Invention

Nanoparticles were prepared comprising a biocompatible lipid, DSPE, conjugated to polyethylene glycol, specifically being 1,2-distearoyl-sn-glycero-3-phosphoethanolamine-N-[methoxy(polyethylene glycol)-2000 (abbreviated as DSPE-mPEG2000) and hydrogenated soy phosphatidylcholine (HSPC). Initially, a variety of lipophilic agents were tested that are known to dissolve in cremaphor, including CsA, paclitaxel, nelfinavir and propofol. Using the protocol described in example 2, we were able to generate the nanoparticles of the invention, however the nanoparticles comprising paclitaxel, nelfinavir or propofol were unstable over a longer period of time. Surprisingly, nanoparticles comprising the macrolide cyclosporine A were stable.

We therefore investigated whether the inclusion of other macrolides could also result in stable nanoparticles. To this end, we selected and tested several other macrolides (sirolimus and tacrolimus). In line with our findings for cyclosporine, nanoparticles comprising lipophilic agent sirolimus or tacrolimus were also stable over a long period of time. Hence, for the production of long-term stable nanoparticles, macrolide lipophilic agents may be preferred, such as CsA, CsA form 2, or cyclosporin B, C, D, E, F, G, H, I, J, K, L, M, N, O, P, Q, R, S, T, U, V, W, X, Y and Z, Voclosporin, Valspodar (PSC833), SCY-635, NIM811, Debio-025, everolimus, ridaforolimus, temsirolimus, umirolimus, zotarolimus, ascomycin, FK1012 or pimecrolimus, or structurally related compounds

Example 2. Method for Preparing the Nanoparticles

A nanoparticle was prepared comprising DSPE-mPEG2000 and HSPC which contains (a mix of) cyclosporine A (CsA) or sirolimus (SIR) or tacrolimus (TAC) and/or palmitoylethanolamide (PEA) as the bioactive lipophilic compounds.

The nanoparticle is formed by weighing e.g. 300 mg of DSPE-mPEG2000, 300 mg of HSPC, 50 mg of PEA and/or 50 mg of CsA/SIR/TAC and dissolving the powders in 1 mL of ethanol. The 1 mL ethanol lipid solution is heated to 60 degrees Celsius and added drop wise to 9 mL of 60 degrees Celsius sterile water. The solution is cooled down to 20 degrees Celsius and residual ethanol is removed upon diafiltration of the particle solution, and subsequently passed through a sterile filtration filter of 0.2 microns. Particle size is determined using dynamic light scattering (zetasizer) and is found to be on average 16 nm.

In a further effort to increase particle and compound concentrations in the final solution, the lipids are dissolved in either one mL of ethanol, isopropanol or methanol, and added to either 9, 5.6, 3 or 1.5 mL of buffer (such as phosphate buffered saline (PBS, pH 7), or an eye drop), resulting in approximately 10, 15, 25 or 40 solvent/buffer percentage, which solvent is essentially lost upon the subsequent diafiltration and sterile filtration steps. Additionally, the DSPE-mPEG2000, CsA/SIR/TAC and/or PEA concentrations are increased in various ratio's to the point that the maximum amount of compound is captured in the nanoparticles without precipitation. After formation of the particles, the formulation strength can be increased by concentrating the solution using diafiltration. Table 1 provides various formulations using different combinations of concentrations (w/w %) of HSPC, mPEG-DSPE, PEA and CsA/SIR/TAC that are obtainable according to the methods described herein. Likewise, the biocompatible lipids (HSPC, mPEG-DSPE) can be substituted by the other herein disclosed biocompatible lipids (such as DLPA, DLPE, DMPA, DMPC, DMPE, DMPG, DMPS, DPPA, DPPC, DPPE, DPPG, DPPS, DSPA, DSPC, DSPE, DSPG or DSPS). Notably, DPPG, HSPG and DMPG could not be easily dissolved in ethanol, while nanoparticles comprising mPEG-DSPE or a mix of mPEG-DSPE and HSPC could be produced in a straightforward manner. Preferred lipids for the production of the nanoparticles of the invention are therefore mPEG-DSPE or a mix of mPEG-DSPE and HSPC. Details of selected nanoparticles are provided in table 1 below.

The lipids may or may not be mixed in different ratios with cholesterol. Nonetheless, the absence of cholesterol is preferred as the addition of cholesterol may result in the production of liposomes instead of the nanoparticles of the invention. The tested bioactive lipophilic compounds (PEA, CsA/SIR/TAC) can be substituted by the other herein disclosed bioactive lipophilic compounds (such as OEA, AEA, or AM, CP, HU, JWH cannaboids, CsA form 2, or cyclosporin B, C, D, E, F, G, H, I, J, K, L, M, N, O, P, Q, R, S, T, U, V, W, X, Y and Z), Voclosporin, Valspodar (PSC833), SCY-635, NIM811, Debio-025, everolimus, ridaforolimus, temsirolimus, umirolimus, zotarolimus, ascomycin, FK1012 or pimecrolimus, or structurally related compounds), or PEG (or PEG substitute) conjugates thereof, to render similar particles.

TABLE 1A

Different compositions of the nanoparticle

| w/w % | HSPC | mPEG-DSPE | CsA/SIR/TAC |
|---|---|---|---|
| 0.1% CsA/SIR/TAC | 0.6 | 0.6 | 0.1 |
| 0.5% CsA/SIR/TAC | 3 | 3 | 0.5 |
| 1% CsA/SIR/TAC | 6 | 6 | 1 |
| 0.1% CsA/0.1% PEA dual-action | 0.6 | 0.6 | 0.1 |
| 0.5% CsA/0.5% PEA dual-action * | 3 | 3 | 0.5 |
| 1% CsA/1% PEA dual-action | 6 | 6 | 1 |
| 0.1% PEA | 0.6 | 0.6 | |
| 0.5% PEA | 3 | 3 | |
| 1% PEA | 6 | 6 | |

TABLE 1B

Appearance of the solution comprising the different nanoparticles

| CsA (mg) *1 | PEA (mg) | HSPC (mg) | mPEG$_{2000}$-DSPE | Appearance |
|---|---|---|---|---|
| | | 200 | 300 | Clear |
| | | 300 | 300 | clear |
| 50 | | 200 | 300 | translucent |
| 250 | | 200 | 300 | Clear |
| | 50 | 200 | 300 | Clear |
| 50 | 50 | 200 | 300 | Clear |
| 50 | 50 | 300 | 300 | Translucent |
| 25 | 25 | 300 | 300 | Translucent |
| 250 | 250 | 1500 | 1500 | Clear |
| 200 | 200 | 4000 | 4000 | clear |

*1 Similar data were obtained for sirolimus or tacrolimus instead of Cyclosporine A.

"Translucent" as indicated in Table 1B means that solution was slightly cloudy, which is a result of the lipids being not completely dissolved and not all lipids having formed a fully transparent nanoparticle solution. In general, the 5:4:6 ratio (lipophilic agent:biocompatible lipid:water soluble polymer) was found to be the most clear.

In the absence of a lipophilic agent, a clear solution comprising the (empty) nanoparticles was obtained when the components mPEG$_{2000}$-DSPE or mEG$_{3400}$-DSPE were used, independent of the ratio HSPC:mPEG-DSPE (see table 1B). A translucent solution was obtained when mPEG$_{5000}$-DSPE was used instead of mPEG$_{2000}$-DSPE or mEG$_{3400}$-DSPE.

A composition comprising a nanoparticle of the invention is a cost-effective, stable, potent (tuneable up to at least 1%), clear, non-stinging, once daily, lubricating, bioactive lipid nanoparticle (15-25 nm) solution comprising a lipophilic agent such as CsA. The properties of the nanoparticle of the invention make it suitable for both anterior and posterior eye diseases. Furthermore, omitting the lipophilic agent from the manufacturing process, and e.g. replacing it by an inert pharmaceutical phospholipid excipient, the product can be applied as a clear Ophthalmic Lipid Solution, both for human and veterinary uses.

Figure 2:
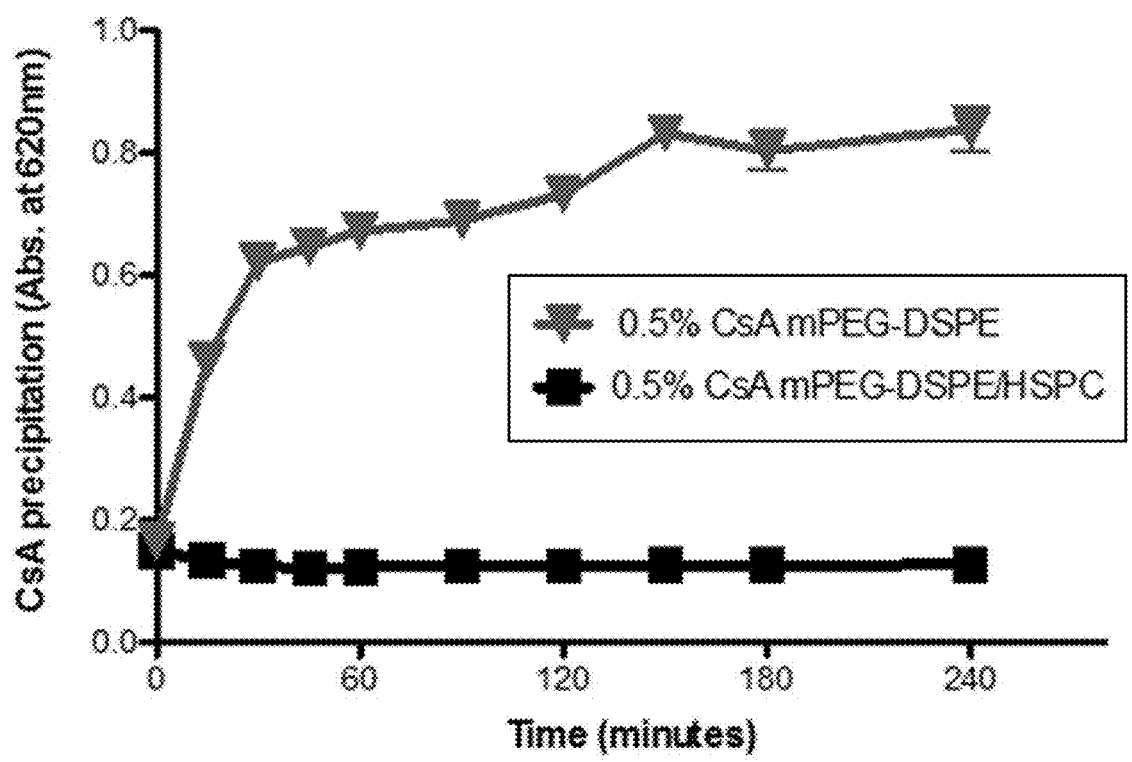
FIG. 2. Outcome of a stability assay of CsA formulations in rat serum at 37 degrees Celsius, in which a 0.5% CsA mPEG-DSPE formulation is demonstrated to precipitate while the same formulation containing additional HSPC was found to be strikingly stable, allowing for improved delivery to tissues and organs.

Example 3. Increased Serum Stability of Phospholipid Containing Nanoparticle Two nanoparticle formulations were prepared comprising a biocompatible lipid, DSPE, conjugated to polyethylene glycol, specifically being 1,2-distearoyl-sn-glycero-3-phosphoethanolamine-N-[methoxy(polyethylene glycol)-2000 (abbreviated as DSPE-mPEG2000) with and without HSPC and with cyclosporine A (CsA) as the bioactive lipophilic compound. Both nanoparticle formulations (with and without HSPC) were diluted 1:1 in rat serum and incubated at 37° C. The absorbance of the mixture was measured at 620 nm. This measurement represents the turbidity of the mixture and the precipitation of cyclosporine A from nanoparticles (FIG. 2). The addition of a phospholipid to the formulation (HSPC) dramatically increased the stability in rat serum. Notably, the 5:4:6 ratio (lipophilic agent:biocompatible lipid:water soluble polymer) was found to be the most stable in these serum tests.

Example 4. Stability of the Nanoparticles

Different biocompatible lipids were tested for their influence on the stability of the nanoparticle. CsA was used as the lipophilic agent in this example, mPEG-DSPE as a water-soluble polymer and either HSPC, SPC or DPPC as biocompatible lipid.

Formulations with SPC or DPPC could be straightforwardly produced and the formed nanoparticles were stable for 1 day. After 1 day, a clear precipitate was visible. The nanoparticles comprising HSPC were stable over a longer period of time.

Without wishing to be bound to any theory, we believe that this surprising difference in stability e.g. between SPC and HSPC may be due to the lower melting point of SPC (below room temperature). We therefore selected HSPC for further testing.

In particular, the stability of nanoparticles HSPC and mPEG-DSPE were tested at 4° C., 20° C. and 60° C. for 1, 3 or 6 months. The nanoparticles were prepared as detailed in example 2. The initial amount of CsA/HSPC/mPEG-DSPE in 1 ml of 96% ethanol was as indicated in table 2 below:

TABLE 2

| Nanoparticle (np) | Nanoparticle components | | |
|---|---|---|---|
| | CsA (mg) | HSPC (mg) | mPEG-DSPE (mg) |
| np-A | — | 240 | 360 |
| np-B | 60 | 240 | 360 |
| np-C | 300 | 240 | 360 |

The compositions were analysed for CsA and lipid content by HPLC. Experiments were performed in triplicate. The results are depicted in table 3 below:

TABLE 3

Stability of the nanoparticles.

| Nanoparticle A | CsA (ng/ml) | HSPC (mg/ml) | mPEG-DSPE (mg/ml) | Size (nm) |
|---|---|---|---|---|
| Production | — | 2.6 | 4.3 | 38.7 (5.9) |
| 3 months (4° C.) | — | 2.1 | 3.8 | |
| 6 months (4° C.) | — | 2.0 | 3.6 | 31.6 (7.5) |
| 3 months (20° C.) | — | 2.3 | 4.1 | |
| 6 months (20° C.) | — | 2.3 | 3.9 | 41.2 (5.6) |

| Nanoparticle B | CsA (ng/ml) | HSPC (mg/ml) | mPEG-DSPE (mg/ml) | Size (St dv) (nm) |
|---|---|---|---|---|
| Production | 1085 | 3.3 | 5.4 | 16.2 (2.6) |
| 3 months (4° C.) | 1048 | 2.9 | 5.2 | |
| 6 months (4° C.) | 845 | 2.8 | 4.8 | 16.8 (3.5) |
| 3 months (20° C.) | 1047 | 3.0 | 5.4 | |
| 6 months (20° C.) | 921 | 3.4 | 5.5 | 16.9 (0.6) |

| Nanoparticle C | CsA (ng/ml) | HSPC (mg/ml) | mPEG-DSPE (mg/ml) | Size (nm) |
|---|---|---|---|---|
| Production | 5793 | 19.9 | 29.3 | 15.5 (2.1) |
| 3 months (4° C.) | 5177 | 13.2 | 24.0 | |
| 6 months (4° C.) | 4751 | 15.3 | 24.7 | 16.9 (0.8) |
| 3 months (20° C.) | 4786 | 14.0 | 25.3 | |
| 6 months (20° C.) | 4867 | 15.0 | 24.4 | 16.9 (0.6) |

Each data point represents the mean of triplicate experiments

CsA concentrations in the formulations decreased, likely due to the precipitation that was observed, in the samples stored at 60° C. for 1 month (data not shown).

As can be seen from Table 3, the nanoparticles remain stable for at least 6 months and stability is maintained when the nanoparticles are stored at 4° C. or at room temperature (20° C.). Hence, the nanoparticles of the invention have a long term stability at 4° C. and 20° C.

Finally, we also tested the stability of nanoparticles comprising a mix of PEA and CsA. Clear solutions could be obtained of which the stability while stored in at 4° C. was at least 8 weeks. The best stability was obtained when using a CsA/PEA/HSPC/mPEG-DSPE ratio of 50:50:300:300 (w/w).

Example 4. Functionality In Vitro of the Nanoparticles of the Invention

CsA binds to the cytosolic protein cyclophilin (immunophilin) of lymphocytes, especially T cells. This complex of CsA and cyclophilin inhibits calcineurin, which, under normal circumstances, is responsible for activating the transcription of interleukin 2 (IL-2). In T-cells, activation of the T-cell receptor normally increases intracellular calcium, which acts via calmodulin to activate calcineurin. Calcineurin then dephosphorylates the transcription factor nuclear factor of activated T-cells (NFATc), which moves to the nucleus of the T-cell and increases the activity of genes coding for IL-2 and related cytokines. In vitro studies have been described were expression and excretion of IL-2 from cells is inhibited by CsA formulations. To show that our CsA from our formulations is active and bioavailable we performed in vitro experiments looking at IL-2 inhibition in Jurkat cells (T-cells). We compared our CsA eye drop formulation (YCU-CsA) with the marketed commercially available eye drop RESTASIS® (Cyclosporine Ophthalmic Emulsion) 0.05%.

The CsA containing nanoparticle was prepared as described in Example 2. The amounts of CsA:HSPC:mPEG-DSPE per 1 ml 96% EtOH was 50:200:300 (mg). Jurkat E6.1 human leukaemic T cells were diluted to $1 \times 10^6$ cells/mL and 150 µL was added per well in a 96-wells cell culture plate. The next day the cells were incubated with different concentrations of the cyclosporine A formulations for 30 minutes and subsequently stimulated with a mixture of PMA/PHA (PMA Sigma-Aldrich P1585, Lectin from *Phaseolus vulgaris* Sigma-Aldrich 61764).

After treatment with PMA/PHA the levels of IL-2 reached >150 pg/mL. Treatment with the CsA formulations decreased the levels of IL-2 and treatment with empty nanoparticles (i.e. not comprising a lipophilic agent) did not have any effect on the IL-2 levels.

The concentration IL-2 in culture medium of the PHA/PMA treated cells was over 90% reduced by cyclosporine A. Notably, The commercially available eye drop Restasis® and the nanoparticle of the invention showed equal reduction of the IL-2 levels, indicating that the nanoparticles are at least as effective as commercially available eye drops. The nanoparticle of the invention is thus fully active without modifying the cyclosporine and need for release from the particle.

Example 5. Functionality In Vivo of the Nanoparticles of the Invention

Safety and Comfort of the Nanoparticles—an Eye Irritation Assay

The safety of selected nanoparticles of the invention were evaluated in vivo. More precisely, the safety (and comfort) levels were tested by directly applying to the eye of mice a composition comprising nanoparticle np-A, np-B or np-C as specified in Example 4 and Table 2 above. Each composition further contained components that are known in the art to be suitable for administration to the eye (trehalose, hypromellose, sodium chloride, boric acid, borate). The mice received four days of four times daily treatment and were evaluated at various time points for irritation.

The different compositions comprising the nanoparticles were compared to borate buffered saline. Only the np-C comprising composition showed a mild lid swelling both pre and post dose on Day 4. The results of this in vivo study indicate that all nanoparticle formulations are comfortable in the eye throughout the entire study in all assessed endpoints (hyperemia, lid swelling, and squinting). These results thus indicate that the nanoparticles are comfortable for use in the eye.

Example 6. Efficacy of the Nanoparticles—a Psoriasis Like Skin Inflammation Study A nanoparticle composition comprising the macrolide tacrolimus was produced as detailed in Example 2. The resulting composition was formulated in a spray suitable for topical delivery on the skin. The efficacy of the produced nanoparticles was subsequently tested in an imiquimod (IMQ)-induced psoriasis-like skin inflammation in mice. To this end, psoriasis-like skin inflammation was induced on the ears and shaved backs of the mice by the daily application of 50 mg of 5% Imiquimod (IMQ) cream. Compared to naïve mice, animals treated with IMQ developed clinical signs of disease including statistically significant increases in psoriasis clinical score and ear thickness over time as well as increased spleen weight (splenomegaly) upon termination of the experiment.

Daily topical treatment with the anti-inflammatory control Clobetasol significantly reduced the psoriasis clinical score (significant by day 3 and throughout the rest of the study), ear thickness (significant by day 5 and throughout the rest of the study) and spleen weight when compared to IMQ-only treated mice. Importantly, treatment with Clobetasol also caused unwanted side effects, such as a significant reduction in body weight.

Treatment with the nanoparticle formulation significantly delayed disease onset, leading to a significantly lower psoriasis clinical score on days 2-8 and significantly less ear thickness on day 5 compared to vehicle treated control mice. Additionally, there was a significant reduction in IMQ-induced splenomegaly in mice treated with the test item compared to vehicle-treated mice, indicating a general reduction in the inflammatory response to IMQ-treatment. Importantly, in contrast to the control compound, the nanoparticles of the invention did not reduce the body weight, indicating that the nanoparticles are well-tolerated.

The therapeutic efficacy of the nanoparticles of the invention is thus not limited to a specific macrolide, such as CsA. Nanoparticles comprising other macrolides, e.g. tacrolimus, are additionally proven to be effective in vivo.

The invention claimed is:

1. A nanoparticle comprising:
    a) two or more phospholipids; and,
    b) at least one acylethanolamide,
    wherein the nanoparticle has a surface comprising a water soluble polymer wherein the water soluble polymer is conjugated to one of the two or more phospholipids.

2. The nanoparticle according to claim 1, wherein the one or more phospholipids are neutral phospholipids.

3. The nanoparticle according to claim 1, wherein the water soluble polymer is at least one of:
    i) a polyalkylether;
    ii) a homopolymer that is a PEG substitute or a PEG alternative;
    iii) a heteropolymer of small alkoxy monomers.

4. The nanoparticle according to claim 3, wherein the water soluble polymer has a molecular weight of at least about 120 Daltons and a polymerization number of at least 6.

5. The nanoparticle according to claim 1, wherein the size of the nanoparticle is between 5-300 nm.

6. A composition comprising a nanoparticle according to claim 1 and an excipient or carrier that is suitable for human or veterinary use.

7. The composition according to claim 6, wherein the composition has a turbidity that is not higher than FTU as determined according to the ISO 7027:1999 standard.

8. The composition according to claim 6, wherein the composition further comprises a substrate for a drug efflux pump.

* * * * *